(12) United States Patent
Kitagawa et al.

(10) Patent No.: US 6,241,886 B1
(45) Date of Patent: Jun. 5, 2001

(54) PLASMA SEPARATION FILTER

(75) Inventors: Tomohiro Kitagawa; Hidehiko Sakurai; Takafumi Hayashi; Makoto Ohno, all of Ohtsu (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 08/665,025

(22) Filed: Jun. 7, 1996

(30) Foreign Application Priority Data

Jun. 9, 1995 (JP) .................................................... 7-143578
Sep. 21, 1995 (JP) .................................................... 7-243480

(51) Int. Cl.[7] ................................................. B01D 29/01
(52) U.S. Cl. .................... 210/507; 210/483; 210/488; 210/489; 210/490; 210/491; 210/503; 210/504; 210/505; 210/506; 210/508
(58) Field of Search .................... 210/435, 446, 210/483, 488, 489, 490, 491, 503, 504, 505, 506, 507, 508

(56) References Cited

U.S. PATENT DOCUMENTS

| | | | |
|---|---|---|---|
| Re. 32,089 | * | 3/1986 | Blatt et al. ............................ 210/651 |
| 4,604,208 | * | 8/1986 | Chu et al. ............................. 210/636 |
| 4,687,580 | * | 8/1987 | Malbrancq et al. ............... 210/433.2 |
| 4,735,726 | * | 4/1988 | Duggins ........................... 210/321.75 |
| 4,845,132 | * | 7/1989 | Masuoka et al. ..................... 210/490 |
| 4,933,092 | * | 6/1990 | Aunet et al. .......................... 210/314 |
| 5,008,012 | * | 4/1991 | Hagihara et al. .................. 210/321.89 |
| 5,135,719 | * | 8/1992 | Hillman et al. ....................... 422/101 |
| 5,139,685 | * | 8/1992 | De Castro et al. ................... 210/505 |
| 5,186,843 | * | 2/1993 | Baumgardner et al. ............. 210/505 |
| 5,262,067 | * | 11/1993 | Wilk et al. ............................ 210/506 |
| 5,364,533 | * | 11/1994 | Ogura et al. .......................... 210/504 |
| 5,423,989 | * | 6/1995 | Allen et al. ........................... 210/505 |
| 5,543,465 | | 8/1996 | Bell et al. ......................... 210/500.41 |
| 5,558,834 | * | 9/1996 | Chu et al. ............................. 210/496 |
| 5,589,399 | * | 12/1996 | Allen et al. ...................... 210/500.21 |
| 5,591,350 | * | 1/1997 | Piechocki et al. .................... 210/764 |
| 5,601,727 | * | 2/1997 | Bormann et al. ..................... 210/767 |
| 5,695,653 | * | 12/1997 | Gsell et al. ........................... 210/767 |

FOREIGN PATENT DOCUMENTS

| | | |
|---|---|---|
| 155 003 | 9/1985 | (EP) . |
| 267 286 | 5/1988 | (EP) . |
| 315 022 | 5/1989 | (EP) . |
| 349 188 | 1/1990 | (EP) . |
| 561 379 | 9/1993 | (EP) . |
| 53-72691 | 6/1978 | (JP) . |
| 57-53661 | 3/1982 | (JP) . |
| 59-214765 | 12/1984 | (JP) . |
| 60-11166 | 1/1985 | (JP) . |
| 60-66164 | 4/1985 | (JP) . |
| 61-38608 | 2/1986 | (JP) . |
| 63-177059 | 7/1988 | (JP) . |
| 64-4790 | 1/1989 | (JP) . |
| 4-208856 | 7/1992 | (JP) . |
| 5-188053 | 7/1993 | (JP) . |
| 5-196620 | 8/1993 | (JP) . |
| 6-96042 | 11/1994 | (JP) . |
| 7-28921 | 4/1995 | (JP) . |

* cited by examiner

Primary Examiner—John Kim
(74) Attorney, Agent, or Firm—Leydig, Voit & Mayer, Ltd.

(57) ABSTRACT

The present invention provides a plasma separation filter capable of easily, speedily and safely separating plasma from a small quantity of blood without damaging blood cell components in the blood. The plasma retains the same protein concentration as in the blood. The present invention also provides a method using such a filter and an apparatus comprising such a filter. The filter of the present invention comprises a micro fiber medium formed of micro fibers with an average hydraulic radius of 0.5 $\mu$m to 3.0 $\mu$m. Such a micro fiber medium is placed in a container having an inlet and an outlet so that a ratio (L/D) of a blood flow passage length (L) to a blood flow passage diameter (D) is 0.15 to 6. The present invention provides such a filter, a plasma separation method using the filter, and a plasma separation apparatus comprising the filter. The present invention can significantly contribute to promote the automation and enhance speediness and safety in clinical tests.

17 Claims, 5 Drawing Sheets

PLASMA SEPARATION FILTER

BACKGROUND OF THE INVENTION

1. Field of the Invention:

The present invention relates to a plasma separation filter, a plasma separation method using the filter and a plasma separation apparatus comprising the filter. More specifically, the present invention relates to a plasma separation filter capable of easily, speedily and safely collecting a small quantity of plasma necessary for blood tests or the like. The plasma contains subtially no blood cells and/or hemoglobin and retains substantially the same composition of protein and electrolytes as in the blood. The present invention also relates to a plasma separation method using the filter and a plasma separation apparatus comprising the filter.

2. Description of the Related Art:

Biochemical tests, which measure components in blood, are widely utilized for diagnosis and observation of progress for a variety of diseases, and occupy an important position as a clinical test. Analysis techniques for the biochemical tests have been significantly developed in recent years. For Example, the development of a variety of automatic analyzers has enabled a number of specimens to be accurately and speedily analyzed.

However, in some biochemical tests, the contamination of erythrocytes or the like interferes with the analysis of a targeted substance. Thus, plasma-or serum which is previously separated from blood is used. The plasma or serum for a test is obtained by collecting blood from a patient, followed by coagulation and centrifugation of the blood cell components. The operation of the coagulation and the centrifugation takes a long period of time, and thus not only prevents the period of time for the clinical test to be shortened, but also requires a large scaled centrifugal machine. Accordingly, except for large hospitals, the clinical test is generally only performed by external laboratories at the present. As a result of such outsourcing of the tests, several days are required to acquire the test results.

Thus, despite the automation of a number of processes for clinical tests, the separation of plasma is still mostly manually performed at the present. Therefore, the operation of separating plasma disadvantageously makes not only the clinical tests inefficient, but also puts a person involved at risk such as infection caused by contacting an infected blood.

A technique generally called dry chemistry is known as a means for solving the above-mentioned problem. According to this technique, when a trace amount of blood is dropped onto a small plate consisting of a serum separation layer formed of a micro fiber filter made of glass fibers or the like and a reaction layer located beneath the serum separation layer, the serum is separated in the serum separation layer. Then, the serum is reacted in the underlying reaction layer and colored, then measured by a spectrophotometer. In such dry chemistry, a liquid type coloring reagent is not used, nor is troublesome serum collection by centrifugation required. Although the dry chemistry is such a simple method, it has the following disadvantages: the number of measurable items is limited when compared with general biochemical analysis and immunological analysis using the liquid type reagent; a number of plates are required in order to test a plurality of items because one plate is used for one test item, thus impairing the advantage of shortening the operation time; and the dry chemistry is expensive. Accordingly, the dry chemistry is not widely used.

One example of means for speedily obtaining plasma is a separation method using membranes. Japanese Laid-Open (Kokai) Publication No. 53-72691 discloses a method for separating plasma from blood by using a fine tube-like filter device (pore diameter: 0.05 to 0.5 $\mu$m) having one closed end as a filter medium. In this method, however, blood cells deposit on the surface of the membrane. Accordingly, a long period of time for filtering plasma is not only required, but also permeability of components such as protein contained in the plasma is poor. On the other hand, when filtering pressure is raised in order to raise a filtering rate, hemolysis (a phenomenon that erythrocyte membranes are ruptured and hemoglobin inside the erythrocyte is released) adversely occurs.

Furthermore, Japanese Laid-Open (Kokai) Publication No. 60-11166 proposes a method in which a filtering cartridge (pore diameter: 0.05 to 1 $\mu$m) employing hollow fiber membranes is used so as to separate plasma from the blood. However, this method requires a priming (wetting the hollow fibers with saline) before separation. Thus, problems arises in that not only the preparing operation before the separation takes more time than the plasma separation itself, but also since the obtained plasma is diluted by the saline, accurate analysis data cannot be obtained.

In the aforementioned separation methods using membranes, a permeability of a relatively large molecular weight substance such as protein in blood is low because the separation is performed based on the molecular size. Thus, a composition of protein contained in plasma does not accurately reflect the original composition of protein in the blood. In addition, when the pore size of the membrane is too large, hemolysis adversely occurs due to erythrocytes clogged.

Other proposed techniques for separating serum or plasma for clinical tests using a fiber filter are as follows. Japanese Laid-Open (Kokai) Publication No. 61-38608 discloses a solid-liquid separation instrument formed of fibers using a volume filtering effect. In the solid-liquid separation instrument, plasma can be obtained by allowing blood to flow through the fibers while applying pressure. However, since pressure loss is large and thus resistance of a filter medium is large, several minutes are required to obtain plasma. In addition, since protein in the blood is adversely adsorbed in the fibers, a concentration of protein in the plasma obtained at an early stage is reduced. Thus, the solid-liquid separation instrument has not been practically used yet.

Japanese Laid-Open (Kokai) Publication Nos. 4-208856 and 5-196620 disclose a separation filter including glass fibers containing polyacrylate derivatives and polyethylene glycol, and lectin impregnated layer, a method for separating and collecting serum or plasma components using the filter and a device for separating serum or plasma using the separation filter. Although these methods and devices can collect serum or plasma for clinical tests without performing centrifugation, the serum or the plasma is obtained in amounts as small as about 100 $\mu$l, and in addition, the period of time required for the separation is about 2 minutes. This is not so different from a period of time required when centrifugation is performed. Furthermore, since these techniques use glass fibers as a separating medium, electrolytes are eluted from glass fibers and blood components are adsorbed to the fibers. As a result, concentrations of electrolytes, phosphorus and lipid in obtained plasma or serum are significantly different from those in the original blood. For this reason, these techniques are not widely used.

As described above, no filter provides satisfactory performance to efficiently and safely separate plasma or serum components for use in clinical tests from a small amount of blood for a short period of time presents a sufficient performance at the present.

SUMMARY OF THE INVENTION

The purpose of this invention includes (1) providing a plasma separation filter capable of easily, speedily and safely separating plasma from blood and excellent in assemblability; (2) providing a method using such a filter; and (3) providing an apparatus comprising such a filter.

According to the present invention, plasma components having the same component composition as in the blood can be obtained without damaging blood cells in the blood. The present invention provides a method for separating blood components using a micro fiber medium. The mechanism of separating plasma using the micro fiber medium according to the present invention is to generate a difference in the moving rates between erythrocytes and plasma moving in the micro fiber medium. The difference in the moving rates is attained by optimizing factors such as materials of the micro fibers, the average fiber diameter and the size of gap between fibers, the length of the blood cell separation layer, the form of the micro fibers, the direction of blood flow, the improvement in the surface of the fibers. As a result, plasma in the blood is separated from the blood components such as erythrocytes and collected. Furthermore, since the pressure loss of the filter of the present invention is low, the blood is speedily treated, and the concentrations of electrolytes and protein in the obtained plasma are substantially the same as that of the blood without separation. Accordingly, the present invention makes it possible to obtain plasma equivalent to the plasma obtained by an ordinary centrifugation. Hereinafter, the present invention will be described in detail.

The present invention relates to a plasma separation filter. The filter according to the present invention comprises a micro fiber medium in a container having an inlet and an outlet, wherein (1) a ratio (L/D) of a blood flow passage length (L) to a blood flow passage diameter (D) of the micro fiber medium is 0.15 to 6; and (2) an average hydraulic radius of the micro fiber medium is 0.5 to 3.0 µm.

In one preferred embodiment, the plasma separation filter comprises the characteristic that when fresh bovine blood having an erythrocyte concentration of 6 to $8\times10^9$/ml is separated at a pressure of 0.2 to 0.4 kg/cm$^2$ and plasma filtrate is collected in an amount equivalent to 10% of a pore volume of the micro fiber medium, (a) a ratio of an erythrocyte concentration in the plasma to the erythrocyte concentration in the blood before the separation is 0.1% or less; and (b) erythrocytes are not substantially hemolyzed.

Furthermore, the plasma separation filter comprises the characteristic that when plasma is collected under the above-mentioned conditions, a difference between an electrolyte concentration in the separated plasma and that in the plasma obtained by centrifugation is less than 10%, or a difference between a protein concentration in the plasma obtained at the start of filtration, that in the plasma obtained at the end of filtration and that in the plasma obtained by centrifugation is less than 10%.

In one preferred embodiment, the micro fiber medium is made of polyester, polypropylene, polyamide, or polyethylene.

In another preferred embodiment, the micro fiber medium is a form of a nonwoven fabric.

In still another preferred embodiment, the single or multilayered nonwoven fabric is placed in the container, and blood flows substantially in parallel to a face of the single or multilayered nonwoven fabric of the micro fiber medium.

In yet another preferred embodiment, the container is a disk-like container, and blood flows from a circumferential portion toward the central portion of the micro fiber medium placed in the container.

Furthermore, the present invention relates to a filter in which a hydrophilic agent is immobilized to the micro fibers.

In one preferred embodiment, the hydrophilic substance is immobilized to the surface of the micro fibers.

In another preferred embodiment, the hydrophilic substance is polyvinyl pyrolidone, and the filter comprises the following characteristic that:

(1) a ratio (L/D) of a blood flow passage length (L) to a blood flow passage diameter (D) of the micro fiber medium is 0.15 to 6; and (2) an average hydraulic radius of the micro fiber medium is 0.5 to 3.0 µm.

In one preferred embodiment, the filter in which the hydrophilic substance is immobilized to the micro fibers comprises the following characteristic that:

when fresh bovine blood having an erythrocyte concentration of 6 to $8\times10^9$/ml is separated at a pressure of 0.2 to 0.4 kg/cm$^2$ and plasma filtrate is collected in an amount equivalent to 10% of a pore volume of the micro fiber medium, (a) a ratio of an erythrocyte concentration in the plasma to the erythrocyte concentration in the blood before the separation is 0.1% or less; and (b) erythrocytes are not substantially hemolyzed.

Furthermore, the plasma separation filter comprises the characteristic that when plasma is collected under the above-mentioned conditions, a difference between an electrolyte concentration in the separated plasma and that in the plasma obtained by centrifugation is less than 10%, or a difference between a protein concentration in the plasma obtained at the start of filtration, that in the plasma obtained at the end of filtration and that in the plasma obtained by centrifugation is less than 10%.

In one preferred embodiment, the micro fiber medium is made of polyester, polypropylene, polyamide, or polyethylene.

In another preferred embodiment, the micro fiber medium is a form of a nonwoven fabric.

In still another preferred embodiment, the single or multilayered nonwoven fabric is placed in the container, and blood flows substantially in parallel to a plane face of the single or multilayered nonwoven fabric of the micro fiber medium.

In yet another preferred embodiment, the container and the nonwoven fabric are shaped like a disk, and the inlet is formed such that blood is supplied across the entire side face of the perimeter of the disk shaped nonwoven fabric, and the outlet is formed such that separated plasma is discharged from the central portion of the disk shaped nonwoven fabric.

Furthermore, the present invention relates to a method for separating plasma using the plasma separation filter comprising the above-mentioned characteristics, or the plasma separation filter in which the hydrophilic substance is immobilized to the micro fibers.

In one preferred embodiment, a filter obtained by placing the single or multilayered nonwoven fabric in the container is used.

In another preferred embodiment, a filter wherein blood flows substantially in parallel to a face of the single or multilayered nonwoven fabric of the micro fiber medium is used. Furthermore, a filter wherein the container is a disk-like container, and blood flows from a circumferential portion toward the central portion of the micro fiber medium placed in the container is used for the method of the present invention.

In still another preferred embodiment, a linear velocity of blood to be treated is 0.05 to 50 cm/min.

Furthermore, the present invention relates to an apparatus comprising the plasma separation filter having the above-mentioned characteristics, or the plasma separation filter in which the hydrophilic substance is immobilized to the micro fibers.

In one preferred embodiment, the apparatus of the present invention further comprises blood supplying means for supplying blood to the filter, pressurizing means for pressurizing the blood supplied to the filter and/or depressurizing means for reducing pressure at the filtrate side in order to separate plasma from the supplied blood, and plasma draining means for draining the separated plasma.

In another preferred embodiment, the apparatus of the present invention further comprises blood and/or hemoglobin detecting means for detecting blood cells and/or hemoglobin in the separated plasma, switching means for fractionating plasma contaminated by blood cells and/or hemoglobin, and blood cell and/or hemoglobin contaminated plasma draining means for draining the fractionated plasma contaminated by blood cells and/or hemoglobin.

In still another preferred embodiment, in the apparatus of the present invention, the filter is releasably provided between the blood supplying means and the plasma collecting means.

In yet another preferred embodiment, the apparatus of the present invention comprises blood supplying means for supplying blood in a predetermined amount, plasma collecting means for collecting plasma in a predetermined amount, or both of the means.

These and other advantages of the present invention will become apparent to those skilled in the art upon reading and understanding the following detailed description with reference to the accompanying figures.

DESCRIPTION OF THE PREFERRED EMBODIMENTS

Figure 1:
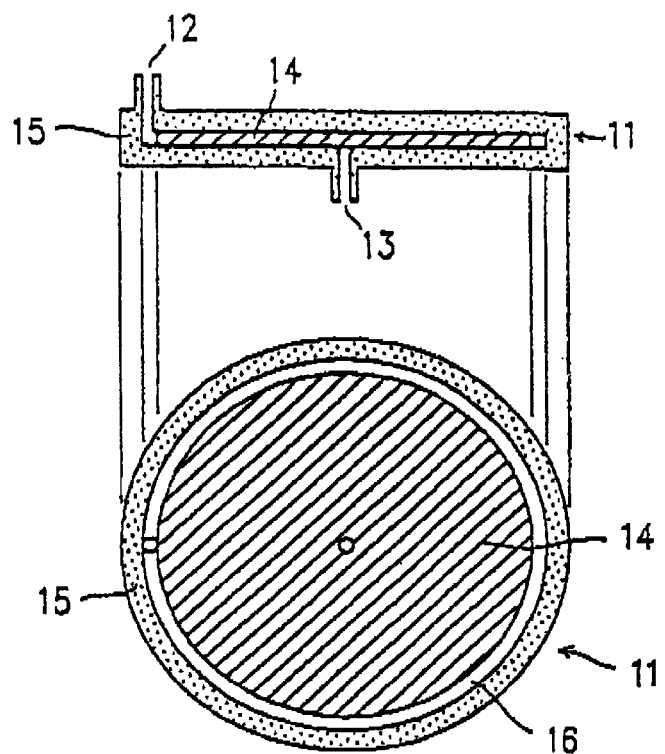
FIG. 1 is a view illustrating an exemplary filter used in a plasma separation apparatus according to the present invention.

The blood used in the present invention generally includes components of blood cells, plasma and the like. The blood can be derived from any origin including a human, a bovine, a goat, a canidae and a rabbit. The blood can be used as it is, or the blood containing an additive such as an anticoagulant and an erythrocyte-agglutinant can be used. Furthermore, in the case where the blood is kept without an anticoagulant, or in the case where a coagulant is added to the blood, fibrinogen in the blood is changed to fibrin, and the coagulation of the blood proceeds. This type of coagulated blood can be also used as it is. Furthermore, the blood which has been subjected to a chemical treatment after centrifugation or the like can be used.

The plasma used in the present invention refers to plasma which contains substantially no blood cell. Thus, the present invention is not limited to plasma which contains strictly no blood cell at all. Furthermore, in the case where the blood is coagulated and then solid components are separated and removed, serum containing no fibrinogen can be obtained. Thus, in the present invention, a term "plasma" includes serum unless it specifically refers to plasma only.

Hereinafter, a plasma separation filter, a plasma separation method and a plasma separation apparatus will be described in this order.

Plasma separation filer

A plasma separation filter of the present invention includes a micro fiber medium and a container having an inlet and an outlet. The micro fiber medium is placed in the container. An average hydraulic radius of the micro fiber medium is preferably 0.5 μm to 3.0 μm, more preferably 0.5 μm to 2.5 μm, and most preferably 0.5 μm to 2.0 μm. Herein, an average hydraulic radius refers to a concept in place of a diameter in the case where a pore of the micro fiber medium does not have a shape of a circle. The average hydraulic radius is defined as follows:

Average hydraulic radius

=Cross-sectional area of tube/circumferential length of the tube

=Volume of liquid in tube/inner surface area of tube in contact with the liquid

=Volume of pore of porous member/surface area of pore of the porous member

According to the present invention, the average hydraulic radius is calculated with the following formula (1):

$$DH = R \times (\rho - rm)/4 \, rm \quad (1)$$

wherein DH indicates an average hydraulic radius of a micro fiber medium in a container (μm), R indicates an average fiber diameter of a micro fiber (μm), p indicates a density of the micro fiber (g/cm³), and rm indicates an average bulk density of the micro fiber medium in a container (g/cm³).

As shown in Formula (1), the average hydraulic radius DH of a micro fiber medium in a container is determined by R and rm in the case where micro fibers made of one type of material are used (i.e., ρ is constant).

In the case where the average hydraulic radius exceeds 3.0 μm, blood cells pass through fiber gaps more easily. Thus, the filter having an average hydraulic radius more than 3.0 μm cannot separate plasma from blood.

In the case where the average hydraulic radius is below 0.5 μm, the fiber gap of the filter, i.e., a flow passage of blood is too narrow, so that blood cells are easily clogged in the flow passages. Furthermore, when the filter is pressurized in order to increase the quantity of the blood passing through, pressure loss is increased and hemolysis easily occurs.

In the average hydraulic radius range of 0.5 μm to 3.0 μm, a smaller average hydraulic radius affects less permeability of components having a small particle diameter such as plasma, at the same time, components having a large particle diameter such as blood cells are difficult to pass through the filter. Thus, the average hydraulic radius is preferably 0.5 μm to 2.8 μm, and most preferably 0.5 μm to 2.0 μm.

Furthermore, the average hydraulic radius of the micro fiber medium of the present invention can be constant in the axis direction from the supply side of blood to the outlet side of plasma, or can be varied depending on the portion of the micro fiber medium. Moreover, the average hydraulic radius can become gradually smaller from the inlet toward the outlet. With such a structure, separation efficiency between blood cell components and plasma components in the vicinity of the outlet can be enhanced.

In the present invention, the average hydraulic radius refers to an average hydraulic radius of the micro fiber medium when the micro fiber medium is placed in a container having an inlet and an outlet, and can be substantially involved in plasma separation. Thus, in the case where a micro fiber medium is used as a base medium 17 for filling a space 16 in FIG. 2, the micro fiber medium used as the base medium 17 (as shown in FIG. 3) is not involved in plasma separation. Accordingly, the average hydraulic radius referred to in the present invention is an average hydraulic radius of the micro fiber medium excluding that used for the base medium 17.

In other words, when all the micro fiber mediums placed in the filter are considered, some micro fiber mediums have average hydraulic radii beyond the preferable range. However, the fact that plasma can be separated even in this case indicates that at least part of the micro fiber mediums placed in the container has an average hydraulic radius in the preferable range.

In the present invention, a prefilter can be provided to remove contaminants in the blood before the micro fiber medium for plasma separation. The average osculum diameter and the average hydraulic radius of the prefilter is naturally larger than the average hydraulic radius of the micro fiber medium. However, when an average hydraulic radius as the entire filter is determined, the average diameter of the prefilter is not considered, but the average hydraulic radius of the main filter should be used.

In the present invention, the micro fiber medium refers to the state where micro fibers are irregularly aggregated. Such a state can be obtained, for example, by compressing, for example, mass, nonwoven, woven, knitted micro fibers independently or in combination. The micro fiber medium is preferably nonwoven fabric or mass of micro fibers in view of moldability, processability, easiness of handling and difficulty of channeling after packed in a container. Particularly, nonwoven fabric is preferable. When the nonwoven fabric is placed in a filter case, uniformity is easily maintained, and sparse portions are unlikely to be generated, whereby blood flow is uniformalized.

A material for the micro fibers is not limited, but examples of the material include polyester, polypropylene, polyamide or polyethylene and the like. The material is preferably hydrophobic polypropylene and polyesters (e.g., polyethylene terephthalate). The above-mentioned materials are preferable because when the materials contact blood or plasma components are not adsorbed to the materials, or a part of the materials is not eluted in the plasma. As described in the section of Prior Art, when plasma or serum separation filter of glass fibers is used, electrolytes are eluted from the glass fibers, or phosphorus or lipid is adsorbed to the glass fibers, so that the resultant substances cannot provide accurate measurement results.

The length of the blood cell separation layer in the present invention is preferably 5 mm or more. The length of the blood cell separation layer refers to the length from the point where the micro fiber medium contacts blood to the point where the blood (plasma) leaves the micro fiber medium. As described above, the present invention utilizes a difference in the moving rates between the blood components in the micro fiber medium to separate plasma from the blood. Pressure is applied from the inlet of the blood separation layer, or pressure is reduced from the outlet thereof, or both of the operations are simultaneously performed so that blood is allowed to flow in the micro fiber medium. Then, blood cell components repeatedly collide with the micro fibers while flowing through the gap of the micro fibers. Adhesive leukocytes and platelets are adsorbed to the micro fibers, and erythrocytes, which is not adhesive, are repeatedly transformed while moving. On the other hand, since plasma is a liquid component, the plasma more rapidly moves through the micro fibers than erythrocytes, and reach the outlet earlier than the erythrocytes. When the length of the blood cell separation layer is 5 mm or less, a sufficient difference in the moving distance between the blood cells and the plasma is not generated. Therefore, the separation between the blood cells and the plasma is insufficient. Thus, the length of 5 mm or less is not preferable. As the length of the blood cell separation layer becomes larger, the efficiency of separation between the blood cells and the plasma becomes higher. On the other hand, problems arise in that pressure loss is raised, or a required amount of micro fiber medium or a required amount of blood is increased. Therefore, the length of the blood separation layer is determined by a required amount of plasma, a blood amount to be used, the limitations of the size of the filters or the like, but the upper limit does not theoretically exist.

In the case where nonwoven fabrics are used, it is preferable that blood flows in parallel to a plane face of the nonwoven fabric (plane face of the stacked nonwoven fabrics). In general, when the nonwoven fabric is used, the direction to which liquid to be treated flows is vertical to the plane face of the nonwoven fabric (plane face of the stacked nonwoven fabrics). However, in the present invention, by allowing blood to flow in parallel to the plane face of the nonwoven fabric, the efficiency of the separation between blood cells and plasma components is enhanced. When blood is allowed to flow in parallel to the face of the nonwoven fabrics, it is believed that the uniformity of the blood flow is improved, because the micro fibers are present without intermittence over the entire flow passage length when the blood flows from the inlet to the outlet. However, the reason why the parallel flow is preferable is not limited to the above-mentioned reason.

The micro fibers to which a hydrophilic substance is immobilized can be preferably used as a filter of the present invention.

The immobilization of the hydrophilic substance can be physically or chemically performed. By immobilizing hydrophilic substance to the surface of the micro fibers, the affinity between the micro fibers and blood is enhanced. Thus, when plasma is separated from the blood, pressure loss can be reduced, and the separation rate can be raised. Any hydrophilic substance can be used, as long as it does not interfere with analysis when it is contaminated into plasma.

Polyvinyl pyrolidone is preferable. Although polyvinyl pyrolidone is eluted to the blood with a relatively low rate because of a relatively large molecular weight, the elution of polyvinyl pyrolidone does not affect the analysis of the blood components. The method for immobilizing polyvinyl pyrolidone is not particularly limited, but any known method can be used. For example, polyvinyl pyrolidone is easily immobilized to the surface of the fibers in such a physical manner that the micro fiber medium is dipped in a solution of polyvinyl pyrolidone, and dried. Furthermore, the micro fiber medium with such polyvinyl pyrolidone physically immobilized on the surface thereof is subjected to a heating treatment, and/or a radiation treatment, so that polyvinyl pyrolidones can be easily crosslinked. The crosslinking can further suppress the elution of polyvinyl pyrolidone to the blood.

The method for the heating treatment is not limited. Examples of the heating method include a method for heating under pressure such as an autoclave treatment, a method for keeping in a tank at a constant temperature and the like. Moreover, the temperature of the heating treatment is not particularly limited, but preferably 70° C. or more, and more preferably 100° C. or more. As the heating temperature is higher, the crosslinking efficiency is improved. The upper limit of the temperature is not simply determined because it depends on the property of the micro fibers to be used or the heat resistance of polyvinyl pyrolidone, but preferably 200° C. or less and more preferably 150° C. or less. A period of time for heating is preferably long so that crosslinking is sufficiently formed, but restricted by the property of the micro fibers to be used or the denaturalization of the polyvinyl pyrolidone. In general, the period of time is preferably in the range of 20 min. to 2 hours. Furthermore, the crosslinking can be formed by heating in both cases where the micro fibers are immersed in the hydrophilic substance solution (WET state), or where the micro fibers are dried after the immersion (DRY state). In either case, polyvinyl pyrolidone can be immobilized to the micro fibers. Unreacted polyvinyl pyrolidone is removed by washing with water.

The method for immobilizing the hydrophilic substance using radiation is not particularly limited. Examples of the method include γ ray irradiation, electron beam irradiation, corona discharge and the like. The γ ray irradiation is preferable in terms of the thickness to be treated and its operatability. An irradiation amount is not particularly limited either, as long as polyvinyl pyrolidone can be sufficiently crosslinked. However, the irradiation amount is preferably in the range of 10 KGy to 50 KGy, because the micro fiber materials and polyvinyl pyrolidone are not denatured by such a radiation in the range. Moreover, the irradiation can be performed in the WET state or DRY state. Unreacted polyvinyl pyrolidone can be removed by washing with water.

A variety of polyvinyl pyrolidone with various molecular weights are available. In order to prevent polyvinyl pyrolidone from being eluted to the blood, polyvinyl pyrolidone having a large molecular weight is particularly preferable.

A filter is produced using a micro fiber medium with the hydrophilic substance immobilized.

The filter is produced by stacking and compressing mass, nonwoven, woven, or knitted micro fibers independently or in combination.

In the present invention, the shape of the container of filters is not particularly limited. Examples of the shape include rectangular parallelopiped, disk, cylinder, truncated cone, fan shape and the like. In the case where a rectangular parallelopiped, disk or fan shaped filter is used to allow the blood to flow in parallel to the face of the micro fiber medium, separation performance can be improved. In the case of a rectangular parallelopiped shaped filter, blood is allowed to flow from one end to the other end of the rectangular parallelopiped. Alternatively, in the case of a disk shaped filter and a fan shaped filter, blood is allowed to flow from the perimeter portion to the central portion. By pressurizing nonwoven fabrics using containers of such shapes, the filter can be sealed. Thus, such shapes are particularly preferable because it is unnecessary to use an adhesive. Particularly, a fan or disk shaped container is more preferable for the following reason: as the blood is moved, the cross-sectional area of the flow passage of the blood becomes gradually smaller. As a result, unevenness of the lateral movement of the blood components is decreased. Especially, the disk shaped container is most preferable in that its operatability is excellent. In the case of the disk shaped container, the nonwoven fabric placed in the container is also shaped like a disk. It is preferable that the inlet for introducing the blood is formed in such a manner that the blood can be supplied across the entire perimeter of the disk shaped nonwoven fabric. For example, a space is provided between the perimeter of the disk shaped nonwoven fabric and the perimeter of the disk shaped container so that one or a plurality of inlets communicating with the space can be provided in the side face, top face or bottom face of the container.

An average fiber diameter of micro fibers used in the filter of the present invention is preferably 0.5 μm to 3.5 μm, more preferably 0.5 μm to 2.8 μm, and most preferably 0.5 μm to 2.0 μm.

The micro fibers having the above-mentioned average fiber diameter can be obtained by an ordinary spinning method such as Meltblow.

Herein, an average fiber diameter of the micro fibers refers to an average value obtained by calculating diameters of 50 micro fibers randomly selected from a photographed micro fiber medium enlarged to a 2000-fold size by a scanning electron microscope, using calipers or a magnifier.

When the average fiber diameter of the micro fibers exceeds 3.5 μm, a length per unit volume of the micro fibers of the micro fiber medium becomes shorter. As a result, the number of intermingled portions in the fibers is reduced, and a fiber gap is enlarged. Accordingly, components having a larger particle diameter such as blood cells are likely to pass through the micro fiber medium, resulting in insufficient separation between blood cells and plasma.

In the case where the average fiber diameter of the micro fibers is less than 0.5 μm, a length per unit volume of the micro fibers becomes longer. As a result, the number of intermingled portions in the fibers is increased, and a fiber gap is reduced. Accordingly, blood cells are likely to be clogged. Furthermore, since pressure loss of the micro fiber medium is increased, hemolysis of erythrocytes is likely to occur.

An average bulk density of the micro fiber medium used in the present invention is preferably 0.15 to 0.60 g/cm$^3$, more preferably 0.18 to 0.50 g/cm$^3$, and most preferably 0.25 to 0.40 g/cm$^3$.

Herein, the average bulk density refers to a value obtained by dividing a weight of the micro fiber medium by a volume of the micro fiber medium.

In the case where the average bulk density is smaller than 0.15 g/cm$^3$, a difference from an as spun average bulk density (e.g., 0.08 g/cm$^3$ to 0.10 g/cm$^3$ in the case of the Meltblow spinning method) of the micro fiber medium is small. As a result, a compression ratio of the micro fiber medium becomes small. Accordingly, dense portions and sparse portions are likely to be generated in the micro fiber medium, resulting in unevenness in moving rates of the blood. In addition, since the fiber gap is averagely large, the separation between blood cells and plasma is insufficient.

In the case where the average bulk density of the micro fiber medium is more than 0.60 g/cm$^3$, a special process such as heating compression is required for producing the micro fiber medium, thus complicating the compression process. Moreover, since the fiber gap of the micro fiber medium becomes small, blood cell components are likely to be clogged in the filter. In addition, since pressure loss of the micro fiber medium is increased, hemolysis is likely to occur.

In the average bulk density range of 0.15 to 0.60 g/cm$^3$, by increasing the average bulk density, the uniformity of the micro fiber medium is further improved, whereas processability is deteriorated. Thus, the average bulk density is preferably 0.18 to 0.50 g/cm$^3$, and most preferably 0.25 to 0.40 g/cm$^3$.

The average bulk density of the micro fiber medium placed in the filter of the present invention can be varied depending on the portion of the filter. For example, the average bulk density can be gradually increased from the inlet to the outlet of the container of the filter. With such a structure, separation efficiency between blood cells and plasma can be higher as the blood components move toward the outlet.

As for a low passage for blood components in the micro fiber medium placed in the filter of the apparatus of the present invention, the ratio (L/D) of a flow passage length (L) to a flow passage diameter (D) is 0.15 to 6, preferably 0.25 to 4, and most preferably 0.5 to 2.

Herein, the flow passage length (L) of the blood components refers to a straight distance in the inside of the micro fiber medium from the point where the blood contacts the micro fibers to the point where plasma leaves the micro fibers (generally, length of the micro fiber medium). The flow passage diameter (D) of the blood components refers to a circle-equivalent diameter of the cross-sectional area on the surface of the micro fiber medium in the inlet portion of the blood extending in the direction perpendicular to the flow passage length.

The circle-equivalent diameter is obtained by using the cross-sectional area (A) in the following formula (2):

$$D=2(A/\pi)^{1/2} \quad (2)$$

Strictly speaking, the micro fiber medium surface has concaves and convexes due to the curve of the micro fibers. However, the cross-sectional area is calculated by ignoring the concaves and convexes and assuming the surface as a plane. In the case where the micro fiber medium has large concaves and convexes formed by surface processing other than those due to the curve of the micro fibers, the cross-sectional area is calculated by averaging the concaves and convexes so as to obtain a plane.

In the case where L/D is smaller than 0.15, the components of the blood move in a short distance because the flow passage is too short. Moreover, since the cross-sectional area is large, moving rates of the components are not uniform in a lateral direction. Thus, the separation between blood cells and plasma is insufficient.

In the case where L/D is larger than 6, separation efficiency is improved. However, since the moving distance is longer, pressure loss is increased. Accordingly, hemolysis is likely to occur.

The filter of the present invention has the following characteristics:

When fresh bovine blood having an erythrocyte concentration of 6 to 8×10$^9$/ml is separated under a pressure of 0.2 to 0.4 Kg/cm$^2$, and at the point where plasma filtrate is collected in an amount equivalent to 10% of a pore volume of the micro fiber medium, (a) the erythrocyte concentration in the plasma is 0.1% or less with respect to the erythrocyte concentration in the blood without separation; and (b) the erythrocytes are not substantially hemolyzed.

Difference between an electrolyte concentration in the separated plasma and that in the plasma obtained by centrifugation is less than 10%.

In the present invention, it is preferable that 90% or more of a concentration of electrolytes in the plasma separated by the plasma separation filter is retained when compared with a concentration of electrolytes in ordinary plasma or serum obtained by centrifugation. Namely, the difference in the electrolyte concentration after the separation by the filter is less than 10% when compared with the separation by centrifugation. Five % or less is more preferable. When the difference in the electrolyte concentration in the plasma exceeds 10%, reliability of a biochemical diagnosis becomes low. Thus, the difference of 10% or more is not preferable. In view of measurement accuracy of biochemical tests, when the difference between the electrolyte concentration in the plasma separated by the filter and that obtained by centrifugation is less than 10%, no problem virtually occurs. The difference of 5% or less presents substantially no problem. Herein, the plasma refers to a supernatant obtained by centrifugation after an anticoagulant is added to the collected blood. Usually, the centrifugation is performed at 1000 G for 10 min.

In the present invention, it is preferable that difference of a protein concentration in the plasma obtained at the start of filtration, at the end of filtration and obtained by centrifugation is less than 10%. Namely, the difference in the protein concentrations after the separation by the filter is less than 10% when compared with the separation by centrifugation. Five % or less is more preferable. When the difference in the protein concentration in the plasma exceeds 10%, reliability of a biochemical diagnosis becomes low. In addition, a value at the early stage of collection may be different from that at the time of completion of the collection, whereby an accurate diagnosis cannot be conducted. Moreover, when the difference in the protein concentrations exceeds 10%, the composition of plasma protein is likely to be significantly changed, thus making it impossible to use in diagnosis of disease. Thus, the difference of less than 10% is preferable, because, generally, the difference of less than 10% does not cause a serious problem in clinical diagnosis, and the difference of 5% or less is in the range of measurement error.

A material of the container of the filter of the present invention is not limited. Examples of the material include metal, glass, plastics such as polyethylene, polypropylene, nylon, polycarbonate, polystyrene, polyester and an ABS resin. In the case where observation of the inside is desired, a transparent or semitransparent material may be selected. Plastics are preferable in view of processability, anti-breakability, and light weight.

Hereinafter, the filter used in the plasma separation apparatus of the present invention will be described with reference to the accompanying drawings.

The filter of the present invention is most simply shown in FIG. 1. In FIG. 1, a filter 11 includes a container 15 having an inlet 12 and an outlet 13, and a disk-like micro fiber medium 14. The micro fiber medium 14 is placed in the container 15. In this filter 11, the micro fibers are compressed in the container 15 so that a suitable space 16 is formed between the inner circumferential surface of the container 15 and the outer circumferential surface of the micro fiber medium 14. The outer circumferential portion of the micro fiber medium 14 can be formed of, for example, a plastic plate having suitable holes capable of passing blood through. When blood is supplied from the inlet 12 of the container located above the circumferential portion of the disk-like micro fiber medium 14, the blood passes through the space 16 so as to be uniformly supplied to the micro fiber medium 14. Then, the blood flows from the outer circumferential portion to the central portion of the micro fiber medium 14. During the course of the flow, plasma and blood cells are separated, and the plasma is collected after being discharged from the outlet 13 in the central portion of the container 15. Hereinafter, the "micro fiber medium 14" refers to the micro fiber medium which is placed in the filter.

Figure 2:
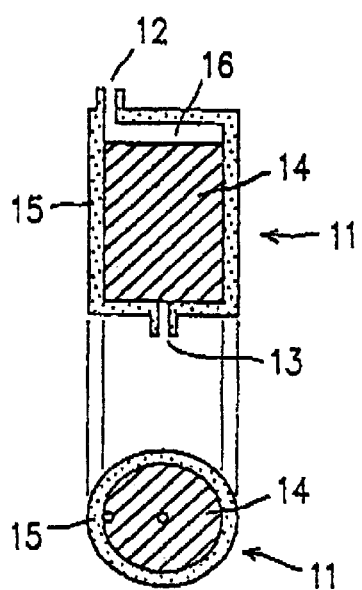
FIG. 2 is a view illustrating an exemplary filter used in a plasma separation apparatus according to the present invention.
Figure 3:
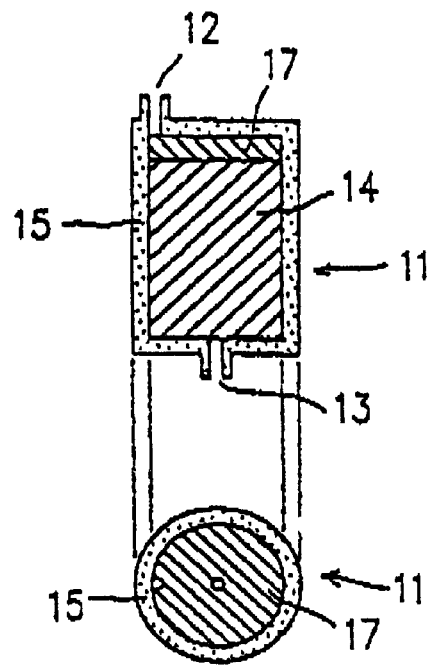
FIG. 3 is a view illustrating the filter in FIG. 2 with a base medium filling a space.

FIG. 2 shows a filter 11 as another embodiment. The filter 11 includes a cylindrical micro fiber medium 14 placed in a cylindrical container 15. Blood is supplied from an inlet 12 of the container 15, and plasma separated by the micro fiber medium 14 is collected after being discharged from an outlet 13 of the container 15. The inlet 12 and the outlet 13 can be located in arbitrary positions.

The filter in FIG. 2 includes a space 16 in the vicinity of the inlet 12, as in the filter in FIG. 1. The space 16 can be provided in order to uniformly perform the supply of blood, pressurization or the like.

A filter 11 in FIG. 3 is a filter including a suitable base medium 17 placed in the space 16 of the filter 11 in FIG. 2. For the base medium 17, any materials can be used, as long as it has larger fiber gaps than the micro fiber medium 14, and all components of the blood can flow therethrough. The base medium can be, for example, a plate-like, paper-like, fiber-like filter medium. In the filter in FIG. 1, the base medium 17 can be placed in the space 16.

Figure 4:
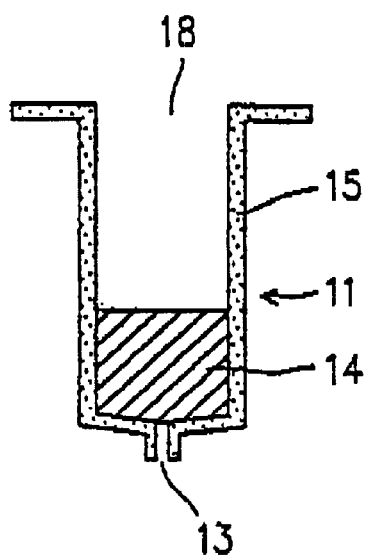
FIG. 4 is a view illustrating an exemplary filter used in a plasma separation apparatus according to the present invention.

A filter 11 in FIG. 4 includes a micro fiber medium 14 in a container 15 having an opening portion 18 and an outlet 13.

The filter 11 can be releasably provided in blood supplying means and/or plasma collecting means described later. As shown in FIGS. 5a and 5b illustrating another embodiment, the container 15 can consist of three portions, i.e., a portion 15a including an inlet 12 or an opening portion 18, a portion including a micro fiber medium 14, and a portion 15b including an outlet 13. Each of the portions can releasably form the container 15. With such a structure, the micro fiber medium portion can be independently exchanged. The exchangeable micro fiber medium can be coated with a blood permeable membrane or the like, and take a form of a releasable cassette capable of being engaged. Examples of the releasable attaching means include engagement, thread and a magnet. The release can be automatically performed.

As described above, in the case where the filter of the present invention is produced by stacking micro fibers, the direction of blood flow can be substantially vertical to the stacked face, or substantially parallel to the stacked face. Suitable shapes for the filter are column or cone-like shape in order to allow blood to flow vertical to the stacked face. By using filters of such shapes, for example, the blood is allowed to flow from the upper portion to the lower portion of the cylindrical filter (FIGS. 2 to 4). Alternatively, the blood is allowed to flow from the bottom to the apex of the cone of the truncated cone. The truncated cone is obtained by cutting off the apex portion in a cone shape. On the other hand, when the filer obtained by stacking the micro fibers to form a disk (e.g., FIG. 1) is used, blood is allowed to flow in parallel to the stacked face from the periphery to the center of the filter. Alternatively, the filter obtained by stacking the micro fibers to form a plane is used, blood is allowed to flow in parallel to the stacked face from one side to the other side of the filter. In the truncated conical or disk-like filter, since the cross-sectional area of the blood flow passage is gradually reduced, moving rates of blood components are raised as the blood moves, and unevenness of movement of the blood components in a lateral direction is reduced. As a result, separation efficiency of the blood is improved.

The plurality of filter of the present invention can be connected. When the filters are connected in series, the separation performance is improved. When the filters are connected in parallel, a quantity of the blood which can be treated is increased.

Furthermore, the filter can be coupled with a sampling container. Such a filter coupled with the sampling container can be.used in an automatic analysis apparatus including means for collecting a predetermined amount of blood and supplying the blood to the filter and means for automatically exchanging the used filter with a new one.

Plasma Separation Method

In order to separate plasma, a pressure loss between an inlet and an outlet is preferably in.the range of 0.03 to 5 $kg/cm^2$. The pressure loss depends on the shape of filters and the treating rate of blood.

In the case where the pressure loss is smaller than 0.03 $kg/cm^2$, load to the blood in the micro fiber medium is small. Thus, when highly hydrophobic micro fibers are used, blood cannot be supplied to the inside of the micro fiber medium. Alternatively, the processing adversely takes too much time. In addition, no difference in the moving rates is generated between blood cell components and plasma components in the micro fiber medium, resulting in insufficient separation of plasma.

In the case where the pressure loss is larger than 5 $kg/cm^2$, the flow rate of the blood is too large. Thus, since plasma and blood cells pass through the micro fiber medium with a small time difference, plasma may be unable to be separated. Moreover, since pressure is applied, erythrocytes may be hemolyzed, or the filter or apparatus may be damaged.

When pressure is raised in the aforementioned range, plasma can be obtained in a larger amount, thus obtaining plasma within a short time period. On the other hand, since hemolysis possibly occurs, the pressure loss is preferably in the range of 0.05 to 3 $kg/cm^2$, and more preferably 0.1 to 1 $kg/cm^2$.

In the plasma separation method according to the present invention, the ratio of the total area of micro fibers to the blood amount to be treated is not limited, but preferably 0.1 to 3 $m^2$ per 1 ml of blood.

In the case where the ratio of the total area of micro fibers to the blood amount to be treated is less than 0.1 $m^2$ per 1 ml of blood, separation efficiency of plasma is deteriorated.

In the case where the ratio of the total area of micro fibers to the blood amount to be treated is greater than 3 $m^2$ per 1 ml of blood, the amount of blood is too small, thus causing a difficulty of supplying the blood and collecting plasma. Moreover, plasma protein is adsorbed to the micro fibers. As a result, the protein components in the plasma may not accurately reflect the protein components in the blood without separation. In addition, pressure loss is easily caused.

When the surface area of the micro fibers is increased, plasma can be obtained in a larger amount. On the other hand, the amount of protein adsorbed to the micro fibers is increased. Thus, the ratio of the total area of micro fibers to the blood amount to be treated is preferably in the range of 0.2 to 2 $m^2$, and more preferably 0.3 to 1.5 $m^2$.

In the plasma separation method of the present invention, linear velocity of treatment of blood is not particularly limited, but typically about 0.05 to 50 cm/min. When the linear velocity is less than 0.05 cm/min., a period of time during which blood components pass through the micro fiber medium is prolonged. As a result, separated plasma and blood cells are diffused during the movement, leading to insufficient separation. when the linear velocity of treatment is greater than 50 cm/min., pressure loss is increased, thus causing hemolysis.

For example, in the case where blood is delivered from the outer circumferential portion of a disk-like container (e.g., FIG. 1) to the central portion, or blood is delivered to the apex of a cone of a conical container, the linear velocity for treatment is varied depending on the portions. In this case, the "linear velocity" refers to an average linear velocity during a period of time from the point when the blood contacts the micro fibers to the point when the plasma (blood) leaves the micro fibers.

In the plasma separation method of the present invention, the. ratio (B/A) or the blood amount for treatment (B) to the pore volume of the micro fiber medium (A) is preferably 0.2 or more. In the case where the ratio is smaller than 0.2 (i.e., the volume of the blood is 20% or smaller than the pore volume), the blood amount is too small, thus causing difficulty in supplying the blood and collecting plasma. Moreover, plasma protein is adsorbed to the micro fibers. As a result, the protein components in the plasma may not accurately reflect the protein components in the blood without separation. The ratio is preferably 0.5 or more, and most preferably 0.7 or more.

In the plasma separation method of the present invention, examples of the method for supplying and pressurizing blood include a piston and pressurized air. In addition, liquid which is not reactive with blood components, for example, liquid with high viscosity for preventing mixing, paraffin, glycerin or the like, is used to push out the blood. The method using pressurized air or paraffin are suitable in the case where the blood amount to be treated is smaller than the pore volume of the micro fiber medium. However, in the case of pressurized air, the blood in the micro fiber medium may be unable to move due to surface tension generated in pores in the micro fiber medium. On the other hand, the method using paraffine or glycerin is suitable in that the problem of the surface tension is not caused.

Plasma Separation Apparatus

The plasma separation apparatus according to the present invention includes a plasma separation filter, preferably blood supplying means for supplying blood to the filter, pressurizing means for pressurizing the supplied blood and/or depressurizing means for reducing pressure at the filtrate side, and plasma draining means for draining the separated plasma. Furthermore, the apparatus can include detecting means for detecting blood cells and/or hemoglobin in the separated plasma, switching means for fractionating plasma contaminated by blood cells and/or hemoglobin, blood cell and/or hemoglobincontaining-plasma draining means for draining plasma contaminated by blood cells and/or hemoglobin, and plasma collecting means for collecting the plasma which has been confirmed not to be contaminated by blood cells and/or hemoglobin. Furthermore, the blood supplying means may supply blood in a predetermined amount, and the plasma collecting means may collect plasma in a predetermined amount. Each of the means will be described below.

<Blood supplying means>

Figure 6:
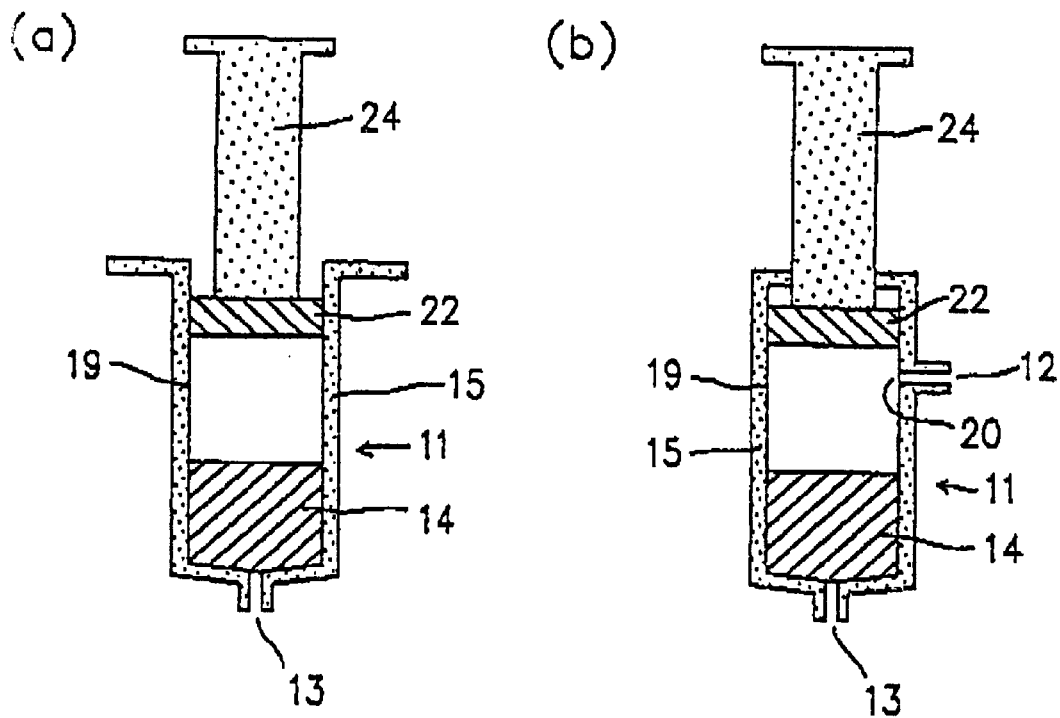
FIGS. 6a and 6b are views illustrating the filters in FIG. 4 further including pressurizing means.

In the apparatus of the present invention, known means can be used as the means for supplying blood to a filter. For example, a pump can be used to supply blood; a container containing blood is pressurized to utilize the pressure for supplying the blood; and the pressure in a filter is reduced to utilize a pressure difference for supplying blood from a blood storage container (e.g., a method using a vacuum pump, or a method in which a piston is moved upward to reduce the pressure in a cylinder and blood is guided from an inlet 12, as shown in FIG. 6b). Needless to say, blood can be manually supplied using a pipet or the like. The means for supplying blood to a filter can be connected to an inlet of the filter. Any methods can be used to connect the means to the filter, as long as it does not allow the blood to leak. For example, the means and the filter is connected by having the outlet of blood of the blood supplying means being engaged, fitted or threaded with the inlet of the filter.

Furthermore, the outlet of the blood supplying means can be tightly closed, and punching means can be provided in the inlet of the filter. On the contrary, the inlet of the filter is tightly closed, punching means can be provided in the blood supplying means. Examples of the punching means include a hollow and tube-like element such as an injection needle. In any cases, punching enables blood to be supplied to the filter. Such connection between the filter and the blood supplying means with punching means is particularly effective to automatically supply blood and avoid the contact with blood. In the case where plasma is to separated from blood collected using a vacuum collecting blood tube which is widely used in recent years, the airtight inlet of the filter is punched and the vacuum collecting blood tube contained in blood is inserted in the punched inlet. By reducing the pressure of the container of the filter, the blood can be supplied to the micro fiber medium in the filter. When the supply of the blood is completed, the vacuum blood collecting tube is extracted, and pressure can be applied from the inlet of the filter.

The blood supplying means can be supplying means for supplying blood in a predetermined amount. For example, an apparatus for supplying blood in a predetermined amount such as a roller pump and a cylinder pump can be used. When blood is supplied in a predetermined amount, the supplying means can be stopped. For example, a sensor can be provided in a blood storage apparatus to measure a reduction in the amount of the blood in blood storage tank and then stop the supplying means.

A volume of blood components to be treated in the apparatus of the present invention (an amount of blood to be supplied by the supplying means) is preferably 20% or more of the pore volume of the micro fiber medium placed in the filter, more preferably 50% or more, and most preferably 70% or more. In the case where the volume of the blood components is less than 20% of the pore volume of the micro fiber medium, it may be difficult to transport the blood into the micro fiber medium, and plasma components are likely to partially remain in the spaces without being collected. Herein, the pore volume (V) of the micro fiber medium placed in the filter is defined as follows:

(V)=Volume of the micro fiber medium−(Total weight of the micro fiber medium/Density of the micro fiber medium)

<Pressurizing means>

Pressure is applied to the blood side (inlet) of the micro fiber medium, and/or pressure is reduced in the permeated liquid side (outlet) so that the blood retained in or supplied to the micro fiber medium is moved to the permeated liquid side, thus causing separation between plasma and blood cells due to a difference in the moving rates between the plasma and the blood cells. At this point, the blood cell components i.e., leukocytes and platelets are adsorbed to the micro fiber medium. A method for applying and reducing pressure is not limited. For example, a pump can be used for pressurization; gas such as pressurized air can be used for pressurization; liquid which is not reacted with the blood components (e.g., paraffine, glycerin or the like) can be pressurized for pushing out the blood; and a vacuum pump or cylinder can be used to suck the blood. The method using paraffine incompatible with the blood components is effective when the amount of blood is small, and preferable because the problem of fluidity due to the surface tension of the blood components is not caused.

FIGS. 6a and 6b show an exemplary plasma separation apparatus including pressurizing means. In the apparatus shown in FIG. 6a, slidable pressurizing means 24 including contact means 22 for tightly contacting an inner wall 19 of a container 15 is inserted from an opening portion 18 of a filter 11. The pressurizing means 24 pressurizes the blood supplied from the opening portion 18. The pressurized blood is separated while passing through a micro fiber medium 14 and plasma is collected from an outlet 13.

The apparatus shown in FIG. 6b includes slidable pressurizing means 24 including a contact means 22 for tightly contacting an inner wall 19 of a container 15 of a filter 11. The apparatus also includes a valve 20 in an inlet 12. When the pressurizing means 24 moved upward, the pressure in the filter is reduced to open the valve 20. As a result, blood is supplied from the inlet 12. Furthermore, when the pressurizing means 24 is moved downward, the valve 20 in the inlet 12 is closed. Then, blood is pressurized and thus plasma is separated. By repeating this procedure, plasma can be continuously separated. Known means can be used for pressurizing the piston.

Figure 7:
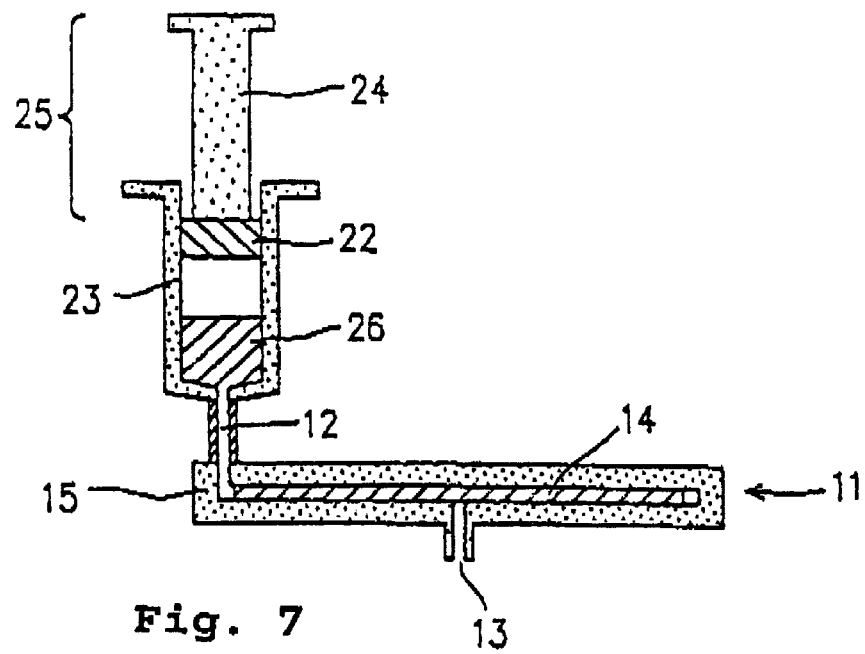
FIG. 7 is a view illustrating an apparatus including the filter in FIG. 1 connected to blood supplying and pressurizing means.

In the apparatus of the present invention, the blood supplying means can be used as the pressurizing means. FIG. 7 shows one example of the case where the blood supplying means is also used as the pressurizing means. In the apparatus shown in FIG. 7, an inlet 12 of a filter 11 is connected to blood supplying means 25. The blood supplying means 25 includes a member 24 having contacting means 22 for tightly contacting an inner wall 23. Blood 26 is stored in the blood supplying means 25. When the member 24 is pushed down, the blood 26 is supplied to the filter 11 and pressurized. Thus, plasma is separated. In this manner, the blood supplying means 25 can also include the pressurizing means 24, and can be used as the pressurizing means. A specific example is a syringe for injection.

In the case where the pressurizing or depressurizing means is used, pressure controlling means for controlling levels of pressurization and depressurization can be included in order to control the moving rates of plasma and blood cells. Pumps are provided before and behind the container of the micro fiber medium to control pressure in order not to cause hemolysis. In this case, the pressures to the blood components before and after passing through the micro fiber medium can be independently controlled. In this case, the levels of pressurization and depressurization can be automatically controlled by a computer or the like.

The pressure loss (a pressure difference between at an inlet and at an outlet of the filter) due to the pressurization and/or depressurization depends on shapes of the micro fiber medium and the treating rate of blood, but preferably 0.03 to 5 $kg/cm^2$, more preferably 0.05 to 3 $kg/cm^2$, and most preferably 0.1 to 1 $kg/cm^2$. In the space where the pressure loss is less than 0.03 $kg/cm^2$, treatment possibly takes more time, or it possibly results in insufficient separation of plasma. When highly hydrophobic micro fibers are used, it may be difficult to transport blood into the micro fiber medium. In the case where the pressure loss is greater than 5 $kg/cm^2$, the time difference for passing through the micro fiber medium between the plasma and blood cells becomes smaller. As a result, plasma can be contaminated by blood cells, thus causing difficulty in collecting the plasma. Moreover, erythrocytes can be hemolyzed, and the apparatus and the micro fiber medium can be damaged.

<Collecting means>

The plasma, which is separated by the micro fiber medium and moves to the permeated liquid side, is then collected for use in tests. Known means can be used as the collecting means. For example, a differential pressure applied to the blood in the filter can be utilized to collect separated plasma in a sample container. Alternatively, a pump can be used to suck the permeated liquid, or push out the permeated liquid to collect the separated plasma in a sample container. The separated plasma can be collected in the sample container immediately below the outlet of the filter. Alternatively, the separated plasma is introduced into the sample container by connecting a hollow tube to the outlet. In the case where the outlet of the filter is connected to the collecting means, the same methods as those for connecting the blood supplying means to the filter can be used herein.

The plasma stored in the sample container or the like is provided as a test sample. Examples of the sample container include a tube and a vial. Any materials can be used for the container, as long as the material of the container does not affect the storage of the obtained plasma. For example, the same material as used for the container for the filter can be used.

In separating plasma by the micro fiber medium, since blood cells are permeated later, the separated plasma can be contaminated by the blood cells. In another case, erythrocytes are destroyed in the micro fiber medium, and the eluted hemoglobin can contaminate the permeated liquid. In separating plasma for clinical tests, the contamination of obtained plasma with blood cells or hemoglobin should be avoided. When plasma is contaminated by blood cells or hemoglobin in a predetermined amount or more, the obtained plasma cannot be used as a clinical test sample.

In order to solve the above-mentioned problem, early permeated liquid (plasma) not containing blood cells can be collected in a preselected amount. For example, plasma is collected in an amount equivalent to 10% of the pore volume of the micro fiber medium under the conditions described in the specification so that plasma containing substantially no blood cells can be obtained. Such an amount can be determined by providing a liquid quantity meter in the plasma collecting container, as in measuring the supplying amount of blood described above. The liquid amount can be measured by detecting with a sensor. After plasma is collected in a predetermined amount, the plasma collecting container is moved to obtain several samples with the same plasma. Such movement can be manually or automatically conducted. In this case, all the plasma can be pooled in one container, and then divided into several other containers with a predetermined amount. Furthermore, the apparatus can be constructed in such a manner that the blood supplying means and the pressurizing means can be stopped when plasma is obtained in a predetermined amount. These means can be controlled by a computer. Alternatively, after plasma is collected in a predetermined amount, further permeated plasma can be disposed of or drained in another container by switching means described later. When blood cell and/or hemoglobin detecting means is provided, the apparatus for determining plasma amount is preferably provided in the vicinity of the outlet leading to a container to drain a blood cell and/or hemoglobin-containing samples, or in a plasma sample container.

<Blood cell and/or hemoglobin detecting means>

As described above, the plasma contaminated by blood cells or the like cannot be used as a test sample. Thus, the apparatus of the present invention can preferably include blood cell and/or hemoglobin detecting means for detecting blood cells and/or hemoglobin in the permeated liquid side. when blood cells and/or hemoglobin are detected, pressurization and thus blood supply are stopped, and the lines are switched so that the draining means can work to drain or dispose of the plasma contaminated. by blood cells and/or hemoglobin. With such a structure, the plasma not contaminated by blood cells or hemoglobin and thus useful as a clinical test sample can be certainly obtained. The plasma with blood cells detected or blood cell components permeated can be returned back to a blood supplying port.

Examples of the means for detecting blood cells and/or hemoglobin in the plasma permeated liquid include optical means and coloring means by chemical reaction. Easily, the optical means can directly detect blood cells and/or hemoglobin. For example, when plasma is contaminated by blood cells, light transmittance is decreased. Alternatively, when plasma is contaminated by hemoglobin, the plasma is colored red. In either case, the detection is performed by the optical means. For example, a leaked blood sensor for detecting leaked blood a predetermined value or more by an optical system can be used. The leaked blood sensor is a sensor for detecting blood cells or hemoglobin in a solution. For example, the absorbance or the transmittance of a predetermined wavelength of the solution is measured by a spectrophotometer. More specifically, by measuring turbidity (e.g., absorbance of a wavelength of 630 nm) due to blood cells in the solution, or the absorbance of hemoglobin (e.g., absorbance of a wavelength of 430 nm), the leakage of blood cells and hemoglobin to the solution can be detected.

A method for coloring by chemical reaction with blood cells and/or hemoglobin can be used as the chromogenic means. The coloring can be detected by the optical means. For example, a method utilizing a peroxidase like function of hemoglobin can be used. Sensitivity can be controlled by selecting suitable peroxide and chromogen.

In view of the objectives of the present invention, any method can be used in addition to the optical method, as long as it can detect blood cells and/or hemoglobin. For example, a cell counter, i.e., a counter for electrically counting the number of cells can be used to detect blood cells.

Among the blood cell and/or hemoglobin detecting means, the optical means can be located at any position between the outlet through which plasma flows and the collecting means. For example, a sensor is externally inserted to directly contact plasma, whereby blood cells and/or hemoglobin can be detected. Alternatively, a sensor is located so that a tube through which plasma flows is interposed between the sensor. Then, light or laser light is emitted at one side of the sensor, and the emitted light is received at the other, thus detecting blood cells and/or hemoglobin. In this case, the tube is preferably transparent so that light can be transmitted. A tube having a low transmissibility can be used, as long as the transmittance of the tube alone is previously measured. Moreover, detecting means by sampling provided in the tube can detect whether the collected plasma is contaminated by blood cells and/or hemoglobin using the chromogenic reagent such as a test paper. When the blood cells and/or hemoglobin are detected, the plasma containing blood cells and/or hemoglobin can be disposed of or drained by switching means. Furthermore, the blood and/or hemoglobin detecting means can be connected to the blood supplying means, the pressurizing means, or the switching means described later, and operated in connection with the processes of the stop of supply or pressurization, disposal or collection by the switching means.

Generally, plasma slightly contains hemoglobin even when hemolysis does not occur, and the concentration is varied with individuals. It is known that when blood is collected using a vacuum blood collecting tube which is widely used in recent years, hemolysis is slightly caused in the collected blood. However, it is known that hemoglobin contained in plasma in such a low concentration does not substantially affect clinical test data. Thus, there exists an acceptable range in which blood cells and/or hemoglobin can be contained in plasma. Accordingly, no serious problems arise, as long as blood cells and/or hemoglobin contained in the plasma are in the acceptable range. For example, an acceptable erythrocyte concentration in obtained plasma is 0.1% or less with respect to the erythrocyte concentration in the blood without separation.

Thus, in the apparatus of the present invention, the blood cell and/or hemoglobin detecting means can be connected to the switching means so that when the blood cell and/or hemoglobin detecting means detects blood cells and/or hemoglobin exceeding a predetermined concentration, the switching means is allowed to operate to dispose of the plasma containing blood cells and/or hemoglobin in a large amount or stop the supply or pressurization of blood.

<Switching means>

Switching means for fractionating plasma contaminated by blood cells and/or hemoglobin is located downstream of the outlet. Examples of the switching means include a switching cock and a switching valve. The switching means can be operated either automatically or manually. In the case where it is automatically operated, the blood cell and/or hemoglobin detecting means is provided at a position before the switching means. The switching means can be coupled with the blood cells and/or hemoglobin detecting means. When a concentration of blood cells and/or hemoglobin exceeds a predetermined value, the switching means is operated by a signal from the blood cell and/or hemoglobin detecting means to switch the line for collecting plasma to the line for draining or disposing of plasma contaminated by blood cells and/or hemoglobin. The plasma collecting method described above can be used as the draining and disposal method.

A separation mechanism of blood cells and plasma in the present invention utilizes the difference in the moving rate between the blood cells and the plasma in the micro fiber medium. The moving rate of plasma in the micro fiber medium is larger than that of blood cells. Thus, by supplying blood to the micro fiber medium and applying pressure, plasma is moved faster than blood cells. Accordingly, after the plasma and the blood cells move in a predetermined distance, they are completely separated. In this manner, since the plasma is first permeated, and then the blood cells permeated, the plasma can be collected utilizing this time difference.

As described above, the present invention is fundamentally different from a centrifugation method utilizing difference in specific gravity between blood components, or a membrane separation method utilizing a difference in size between the blood components. Furthermore, the present invention is different from a separation method for leukocytes utilizing only adsorption of the blood components to the micro fibers.

The plasma separation apparatus of the present invention utilizes a difference in the moving rates between plasma and blood cells. Thus, the obtained plasma components will not have been diluted, or the components not changed. As a result, the plasma is the same as the plasma obtained by centrifugation. Furthermore, means for detecting blood cell and/or hemoglobin and a cock operated in connection therewith are provided in the permeated side so that the contamination of a plasma sample with blood cells and/or hemoglobin can be prevented. According to the apparatus of the present invention, a plasma sample not contaminated by blood cells and/or hemoglobin can be easily, speedily and safely obtained. Thus, the apparatus of the present invention is useful in the field where plasma should be separated from a small amount of blood in a short period of time for use in a clinical test. Furthermore, the apparatus of the present invention can realize automation of collecting a plasma sample for a clinical test, thus significantly contributing to promote the automation, speediness and safety.

EXAMPLES

In Examples, a nonwoven fabric formed of micro fibers (density: 1.38 g/cm$^3$) made of polyethylene terephthalate obtained by spinning by an ordinary Meltblow method was used as a micro fiber medium. As a bovine blood, fresh bovine blood within 8 hours after collected was used. An anticoagulant (ACD: citric acid dextrose) was added immediately after collecting the blood in order to prevent the blood from coagulating. An erythrocyte concentration in the bovine blood was 7.2 ×10$^9$/ml, a leukocyte concentration was 6.8×10$^6$/ml, and a platelet concentration was 2.1×10$^8$/ml.

The performance of a plasma separation filter was evaluated by analyzing concentrations of blood cells (erythrocytes, leukocytes and platelets) contained in plasma, the presence or absence of hemolysis and blood components (serum amylase, total cholesterol, neutral fat, urea nitrogen, blood sugar, total protein concentration and albumin). The plasma obtained by centrifuging the above-mentioned bovine blood was used for comparison.

The concentration of blood cells contained in plasma was measured with a Coulter counter method. The upper limit concentration of detecting erythrocytes was 2×10$^5$/ml, that for leukocytes was 1×10$^5$/ml, and that for platelets was 1×10$^6$/ml.

Hemolysis was detected by measuring a concentration of hemoglobin contained in plasma using an O-toluidine method.

Analysis of each blood components was performed in the following method:
1. Serum amylase: G5CNP method
2. Total cholesterol: cholesterol oxidase-peroxidase coloring method
3. Neutral fat: LPL-glycerol-3-phosphate oxidase-peroxidase coloring method
4. Urea nitrogen: urease-indophenol method
5. Blood sugar: glucose oxidase-peroxidase coloring method
6. Total protein concentration: Buret method
7. Albumin: BCG (Brom Cresol Green) method

Example 1

A plasma separation filter as shown in FIG. 1 was produced in the following manner: A disk-like container with a diameter of 52.0 mm and a thickness of 2.0 mm was made from acrylic polymer. The container had a hole with a diameter of 1.0 mm on the top end portion for working as an inlet, and a hole with a diameter of 1.0 mm on the central portion of the bottom for working as an outlet. As a micro fiber medium, 14 sheets of nonwoven fabrics (50 g/m$^2$, thickness of about 2 mm) formed of micro fibers made of polyethylene terephthalate of an average fiber diameter of 1.8 μm were stacked in the container so that a resultant multilayer has a weight of 1.4 g, a diameter of 50.0 mm and a thickness of 2.0 mm. At the same time, a space having a width of 1.0 mm was provided between the outer surface of the micro fiber medium and the inner surface of the container. In the produced filter, a volume of the micro fiber medium was about 3.9 cm$^3$, and a volume of the space was about 0.32 cm$^3$. The total surface area of the micro fibers in the plasma separation filter, the average bulk density, the average hydraulic radius and the pore volume and L/D of the micro fiber medium are shown in Table 1. Each value was calculated in the following formulae. The density of polyethylene terephthalate was 1.38 g/cm$^3$ described above.

Total surface area
=4×weight of micro fiber medium/(density of micro fibers x average fiber diameter)
=4×1.4 g/(1.38 g/cm$^3$×1.8 μm)=2.3 m$^2$ Average bulk density
=weight of micro fiber medium/volume of micro fiber medium
=1.4 g/3.9 cm$^3$ =0.36 g/cm$^3$ Average hydraulic radius
=average fiber diameter×(density of micro fibers−average bulk density)/(4×average bulk density)
=1.8 μm×(1.38 g/cm$^3$−0.36 g/cm$^3$)/(4×0.36 g/cm$^3$)=1.28 μm Pore Volume
=Volume of micro fiber medium−(weight of micro fiber medium/density of micro fibers)
=3.9 cm$^3$−(1.4 g÷1.38 g/cm$^3$)=2.9 cm$^3$ L/D (flow passage length of blood components/flow passage diameter of blood components)
=L/2 (cross sectional area of micro fiber aggregate surface at blood inlet portion/π)$^{0.5}$
=(2.5 cm)/2((5.0 cm×π×0.2 cm)÷π)$^{0.5}$
=1.25

The bovine blood was injected in an amount 4 ml from the inlet of the container of the plasma separation filter to fill the space between the outer surface of the micro fiber medium and the inner surface of the container, and then a pressure of 0.2 kg/cm$^2$ was applied to push out the bovine blood. The bovine blood entered from the outer surface of the micro fiber medium and moved from the outer portion to the center portion of the inside of the micro fiber medium in a horizontal direction. After 20 seconds passed from the start of the pressurization, permeation of plasma from the outlet of the container was started. Then, 4 seconds later, the contamination of erythrocytes in the liquid occurred. Thus, the plasma was collected for about 2 seconds from the start of the permeation, thus obtaining 0.29 ml of plasma. An average linear velocity for treatment was 75 mm/min. (=25 mm/20 sec.).

The concentrations of erythrocytes, leukocytes, and platelets in the plasma of 0.29 ml obtained above were below the detection limit. Thus, the ratio of the erythrocyte concentration in the obtained plasma to erythrocyte concentration in the bovine blood without the separation (hereinafter, referred to as an erythrocyte contamination ratio) was 0.003% (=(2×10$^5$÷7.2×10$^9$)×100) or less. The hemoglobin concentration in the obtained plasma was 5 mg/dl, and the analysis results of the blood components are shown in Table 1.

Example 2

A plasma separation filter was produced in the same manner as in Example 1, except that a filling amount of the nonwoven fabrics was 0.8 g (a multilayer of 8 fabrics).

The total surface area of the micro fibers in the plasma separation filter, the average bulk density, the average hydraulic radius and the pore volume and L/D of the micro fiber medium are shown in Table 1.

The plasma separation was performed using the plasma separation filter in the same manner as in Example 1. After 15 seconds passed from the start of the pressurization, permeation of plasma was started. Then, 2 seconds later, the contamination of erythrocytes in the liquid occurred. Thus, the plasma was collected for about 1.5 seconds from the start of the permeation, thus obtaining 0.33 ml of plasma. An average linear velocity for treatment was 100 mm/min.

The concentrations of leukocytes and platelets in the plasma of 0.33 ml obtained above were below the detection limit. The concentration of erythrocytes was 3×10$^5$/ml. Thus, the erythrocyte contamination ratio was 0.004%. The hemoglobin concentration in the obtained plasma was below the detection limit, and the analysis results of the blood components are shown in Table 1.

Example 3

A plasma separation filter as shown in FIG. 3 was produced in the following manner: A column-like container with a diameter of 29.0 mm and a thickness of 6.5 mm was made from polypropylene. The container had a hole with a diameter of 1.0 mm on the top end portion for working as an inlet, and a hole with a diameter of 1.0 mm on the central portion of the bottom for working as an outlet. As a micro fiber medium, 12 sheets of nonwoven fabrics (50 g/m$^2$, thickness of about 3 mm) formed of micro fibers made of polyethylene terephthalate of an average fiber diameter of 1.8 μm were stacked in the container so that a resultant multilayer has a weight of 1.2 g, a diameter of 29.0 mm and a thickness of 6.0 mm, and a space having a width of 0.5 mm was provided between the top surface of the micro fiber medium and the inner top surface of the container. The space was filled with 2 nonwoven fabrics (50 g/m$^2$, thickness of about 1 mm) having a weight of 0.33 g formed of micro fibers made of polyethylene terephthalate of an average fiber diameter of 10 μm. Thus, a plasma separation filter was produced (a volume of the micro fiber medium: about 4.0 cm$^3$; a volume of the space: about 0.33 cm$^3$).

The total surface area of the micro fibers in the plasma separation filter, the average bulk density, the average hydraulic radius and the pore volume and L/D of the micro fiber medium are shown in Table 1.

The bovine blood was injected in an amount 4 ml from the inlet of the container of the plasma separation filter to fill the space between the top surface of the micro fiber medium and the inner top surface of the container, and then a pressure of 0.4 kg/cm$^2$ was applied to push out the bovine blood. The bovine blood was entered from the top surface of the micro fiber medium and moved downward through the inside of the micro fiber medium. After 30 seconds passed from the start of the pressurization, permeation of plasma from the outlet of the container was started. Then, 5 seconds later, the contamination of erythrocytes in the permeated liquid occurred. Thus, the plasma was collected for about 3 seconds from the start of the permeation, thus obtaining 0.31 ml of plasma. An average linear velocity for treatment was 12 mm/min.

The concentrations of blood cell components contained in the plasma of 0.31 ml obtained above were all below the detection limit. Thus, the erythrocyte contamination ratio was 0.003% or less. The hemoglobin concentration in the obtained plasma was 8 mg/dl, and the analysis results of the blood components are shown in Table 1.

Example 4

A plasma separation filter as shown in FIG. 1 was produced in the following manner: A disk-like container with a diameter of 134 mm and a thickness of 0.30 mm was made from acrylic polymer. The container had a hole with a diameter of 1.0 mm on the top end portion for working as an inlet, and a hole with a diameter of 1.0 mm on the central portion of the bottom for working as an outlet. As a micro fiber medium, 3 nonwoven fabrics (50 g/m$^2$, thickness of about 2 mm) formed of micro fibers made of polyethylene terephthalate of an average fiber diameter of 3.0 μm were stacked in the container so that a resultant multilayer has a weight of 2.0 g, a diameter of 130 mm and a thickness of 0.30 mm. At the same time, a space having a width of 2.0 mm was provided between the outer surface of the micro fiber medium and the inner surface of the container. In this manner, the plasma separation filter shown in FIG. 1 was produced (a volume of the micro fiber medium: about 4.0 cm$^3$, and a volume of the space: about 0.25 cm$^3$).

The total surface area of the micro fibers in the plasma separation filter, the average bulk density, the average hydraulic radius and the pore volume and L/D of the micro fiber medium are shown in Table 1.

The plasma separation was performed using the plasma separation filter in the same manner as in Example 1, except that a pressure of 0.4 kg/cm$^2$ was applied to push out the bovine blood. After 120 seconds passed from the start of the pressurization, permeation of plasma was started. Then, 18 seconds later, the contamination of erythrocytes in the permeated liquid occurred. Thus, the plasma was collected for 12 seconds from the start of permeation, thus obtaining 0.26 ml of plasma. An average linear velocity for treatment was 32.5 mm/min.

The concentrations of leukocytes and platelets in the plasma of 0.26 ml obtained above were below the detection limit. The concentration of erythrocytes was 2.9×10$^8$/ml. Thus, the erythrocyte contamination ratio was 0.04%. The hemoglobin concentration in the obtained plasma was 4 mg/dl, and the analysis results of the blood components are shown in Table 1.

Example 5

A plasma separation filter as shown in FIG. 2 was prepared in the following manner: A column-like container with a diameter of 15.2 mm and a thickness of 24 mm was made from polypropylene. The container had a hole with a diameter of 1.0 mm on the top end portion for working as an inlet, and a hole with a diameter of 1.0 mm on the central portion of the bottom for working as an outlet. As a micro fiber medium, mass of micro fibers made of polyethylene terephthalate with an average fiber diameter of 1.8 μm was placed in the container so that the micro fiber medium has a weight of 1.4 g, a diameter of 15.2 mm and a thickness of 22 mm, and a space having a width of 2.0 mm was provided between the top surface of the micro fiber medium and the inner top surface of the container. Thus, a plasma separation filter was produced (a volume of the micro fiber medium: about 4.0 cm$^3$; a volume of the space: about 0.36 cm$^3$).

The total surface area of the micro fibers in the plasma separation filter, the average bulk density, the average hydraulic radius and the pore volume and L/D of the micro fiber medium are shown in Table 1.

The bovine blood was injected in an amount 4 ml from the inlet of the container of the plasma separation filter to fill the space between the top surface of the micro fiber medium and the inner top surface of the container, and then a pressure of 0.4 kg/cm$^2$ was applied to push out the bovine blood. The bovine blood entered from the top surface of the micro fiber medium and moved downward through the inside of the micro fiber medium. After 300 seconds passed from the start of the pressurization, permeation of plasma was started. Then, 70 seconds later, the contamination of erythrocytes in the permeated liquid occurred. Thus, the plasma was collected for about 30 seconds from the start of permeation, thus obtaining 0.30 ml of plasma. An average linear velocity for treatment was 4.4 mm/min.

The concentrations of blood cell components contained in the plasma of 0.30 ml obtained above were all below the detection limit. Thus, the erythrocyte contamination ratio was 0.003% or less. The hemoglobin concentration in the obtained plasma was 6 mg/dl, and the analysis results of the blood components are shown in Table 1.

Example 6

A plasma separation filter was produced in the same manner as in Example 3, except that mass of micro fibers made of polyethylene terephthalate of an average fiber diameter of 0.8 μm was used as the micro fiber medium.

The total surface area of the micro fibers in the plasma separation filter, the average bulk density, the average hydraulic radius and the pore volume and L/D of the micro fiber medium was the same as in Example 3, as shown in Table 1.

The plasma separation was performed using the plasma separation filter in the same manner as in Example 3. After 880 seconds passed from the start of the pressurization, permeation of plasma was started. Then, 115 seconds later, the contamination of erythrocytes in the permeated liquid occurred. Thus, the plasma was collected for about 90 seconds from the start of the permeation, thus obtaining 0.31 ml of plasma. An average linear velocity for treatment was 0.41 mm/min.

The concentrations of blood cell components in the plasma of 0.31 ml obtained above were all below the detection limit. Thus, the erythrocyte contamination ratio was 0.003% or less. The hemoglobin concentration in the obtained plasma was 10 mg/dl, and the analysis results of the blood components are shown in Table 1.

Example 7

A plasma separation filter was produced in the same manner as in Example 5, except that: a container with a diameter of 10.0 mm and a thickness of 55.0 mm was used; as micro fiber medium, mass of micro fibers of an average fiber diameter of 3.2 μm was placed in an amount of 2.0 g in the container so that the micro fiber medium had a diameter of 10.0 mm and a thickness of 51.0 mm; and a space having a thickness of 4.0 mm was provided between the top surface of the micro fiber medium and the inner top surface of the container. Thus, a plasma separation filter was produced (a volume of the micro fiber medium: about 4.0 cm$^3$; a volume of the space: about 0.31 cm$^3$).

The total surface area of the micro fibers in the plasma separation filter, the average bulk density, the average hydraulic radius and the pore volume and L/D of the micro fiber medium are shown in Table 1.

The plasma separation was performed using the plasma separation filter in the same manner as in Example 5. After 264 seconds passed from the start of the pressurization, permeation of plasma was started. Then, 25 seconds later, the contamination of erythrocytes in the permeated liquid occurred. Thus, the plasma was collected for about 22 seconds from the start of the permeation, thus obtaining 0.26 ml of plasma. An average linear velocity for treatment was 11.6 mm/min.

The concentrations of leukocytes and platelets in the plasma of 0.26 ml obtained above were all below the detection limit. The concentration of erythrocytes was 4.3×10$^8$/ml. Thus, the erythrocyte contamination ratio was 0.06%. The hemoglobin concentration in the obtained plasma was below the detection limit, and the analysis results of the blood components are shown in Table 1.

Example 8

A plasma separation filter was made in the same manner as in Example 5, except that the filling amount of the mass of the micro fibers was 0.8 g. The total surface area of the micro fibers in the plasma separation filter, the average bulk density, the average hydraulic radius and the pore volume and L/D of the micro fiber medium are shown in Table 1.

The plasma separation was performed using the plasma separation filter in the same manner as in Example 5. After 150 seconds passed from the start of the pressurization, permeation of plasma was started. Then, 20 seconds later, the contamination of erythrocytes in the permeated liquid occurred. Thus, the plasma was collected for about 17 seconds from the start of the permeation, thus obtaining 0.34 ml of plasma. An average linear velocity for treatment was 8.8 mm/min.

The concentrations of l.eukocytes and platelets in the plasma of 0.34 ml obtained above were all below the detection limit. The concentration of erythrocytes was 2.2×10$^8$/ml. Thus, the erythrocyte contamination ratio was 0.03%. The hemoglobin concentration in the obtained plasma was below the detection limit, and the analysis results of the blood components are shown in Table 1.

Comparative Example 1

A plasma separation filter was produced in the same manner as in Example 1, except that 8 sheets of nonwoven fabrics (50 g/m$^2$; a thickness: 2 mm) formed of micro fibers of an average fiber diameter of 2.5 μm was used as the micro fiber medium to be placed in an amount of 0.8 g in the container. The total surface area of the micro fibers in the plasma separation filter, the average bulk density, the average hydraulic radius and the pore volume and L/D of the micro fiber medium are shown in Table 1.

The plasma separation was performed using the plasma separation filter in the same manner as in Example 1. After 10 seconds passed from the start of the pressurization, the permeation of liquid was started. The permeated liquid was contaminated by blood cells from the beginning. Thus, the permeated liquid was collected for about 1.0 second from the start of permeation, thus obtaining 0.33 ml of the permeated liquid.

The concentrations of leukocytes and platelets in the permeated liquid of 0.33 ml obtained above were below the detection limit. However, the concentration of erythrocytes was $3.8 \times 10^8$/ml. Thus, the erythrocyte contamination ratio was 5.3%. The hemoglobin concentration in the permeated liquid obtained was below the detection limit. The analysis results of the blood components are omitted.

Comparative Example 2

A plasma separation filter was produced in the same manner as in Example 1, except that 20 sheets of nonwoven fabrics (50 g/m$^2$; a thickness: 2 mm) formed of micro fibers of an average fiber diameter of 1.0 μm were used as the micro fiber medium to be placed in an amount of 2.0 g in the container. The total surface area of the micro fibers in the plasma separation filter, the average bulk density, the average hydraulic radius and the pore volume and L/D of the micro fiber medium are shown in Table 1.

The plasma separation was performed using the plasma separation filter in the same manner as in Example 1, except a pressure of 0.4 kg/cm$^2$ was applied. After 1365 seconds passed from the start of the pressurization, the permeation of liquid was started. The permeated liquid was colored red from the beginning. Thus, the permeated liquid was collected for about 1600 seconds from the start of the permeation, thus obtaining 0.26 ml of permeated liquid.

The concentrations of blood cell components in the permeated liquid of 0.26 ml obtained above were all below the detection limit. The hemoglobin concentration in the plasma in the obtained permeated liquid was 95 mg/dl. The analysis results of the blood components are omitted.

Comparative Example 3

A plasma separation filter was produced in the same manner as in Example 3, except that: a column-like container with a diameter of 50.0 mm and a thickness of 2.3 mm was made from acrylic polymer; as a micro fiber medium, 14 sheets of nonwoven fabrics (50 g/m$^2$, thickness of about 1 mm) formed of micro fibers made of polyethylene terephthalate with an average fiber diameter of 1.8 μm were stacked in the container so that a resultant multilayer has a weight of 1.4 g, a diameter of 50.0 mm and a thickness of 2.0 mm, and a space having a width of 0.3 mm was provided between the top surface of the micro fiber medium and the inner top surface of the container; the space was filled with a nonwoven fabric (50 g/m$^2$, thickness of about 1 mm) with a weight of 0.17 g formed of micro fibers made of polyethylene terephthalate with an average fiber diameter of 10 μm. Thus, a plasma separation filter was produced (a volume of the micro fiber medium: about 3.9 cm$^3$; a volume of the space: about 0.59 cm$^3$).

The total surface area of the micro fibers in the plasma separation filter, the average bulk density, the average hydraulic radius and the pore volume and L/D of the micro fiber medium are shown in Table 1.

The plasma separation was performed using the plasma separation filter in the same manner as in Example 3. After 15 seconds passed from the start of the pressurization, the permeation of liquid was started. The permeated liquid was contaminated by blood cells from the beginning. Thus, the permeated liquid was collected for about 1.5 seconds from the start of the permeation, thus obtaining 0.30 ml of permeated liquid.

The concentrations of leukocytes and platelets in the permeated liquid of 0.30 ml obtained above were below the detection limit. However, the concentration of erythrocytes was $6.9 \times 10^9$/ml. Thus, the erythrocyte contamination ratio was 55%. The hemoglobin concentration in the plasma in the obtained permeated liquid was below the detection limit. The analysis results of the blood. components are omitted.

Comparative Example 4

A plasma separation filter was produced in the same manner as in Example 5, except that: a container with a diameter of 8.0 mm and a thickness of 86.0 mm was made from polypropylene; the micro fiber medium was placed in the container to have a diameter of 8.0 mm, a thickness of 80.0 mm and a space with a thickness of 6.0 mm provided between the top surface of the micro fiber medium and the inner top surface of the container. Thus, a plasma separation filter was produced (a volume of the micro fiber medium: about 4.0 cm$^3$; a volume of the space: about 0.30 cm$^3$). The total surface area of the micro fibers in the plasma separation filter, the average bulk density, the average hydraulic radius and the pore volume and L/D of the micro fiber medium are shown in Table 1.

The plasma separation was performed using the plasma separation filter in the same manner as in Example 5. After 1920 seconds passed from the start of the pressurization, the permeation of liquid was started. The permeated liquid was colored red from the beginning. Thus, the permeated liquid was collected for about 3600 seconds from the start of the permeation, but as little as 0.25 ml of permeated liquid was obtained.

The concentrations of blood cell components in the permeated liquid of 0.25 ml obtained above were all below the detection limit. The hemoglobin concentration in the plasma in the obtained permeated liquid was 75 mg/dl. The analysis results of the blood components are omitted.

Comparative Example 5

The same plasma separation filter as obtained in Example 1 was produced, and the plasma separation was performed in the same manner as in Example 1, except that the bovine blood was used in an amount of 0.5 ml.

Even when all the blood was supplied into the micro fibers, liquid was not permeated. Thus, pressurized air was further supplied from the inlet of the container. However, the pressurized air passed through the micro fibers faster than the blood. Accordingly, only bubbles of blood containing air were obtained at the outlet. It is believed that this was because the blood amount was too small for the 3.0 ml of pore volume of the micro fiber medium so that the blood was not uniformly distributed.

Comparative Example 6

A plasma separation filter was produced in the same manner as in Example 3, except that: a container with a diameter of 35.0 mm and a thickness of 4.6 mm was made from polypropylene; as a micro fiber medium, 18 nonwoven fabrics (50 g/m$^2$, thickness of about 1 mm) formed of micro fibers made of polyethylene terephthalate with an average fiber diameter of 1.8 μm were stacked in the container so that a resultant multilayer has a weight of 0.87 g, a diameter of 35.0 mm and a thickness of 4.2 mm, and a space having a thickness of 0.4 mm was provided between the top surface of the micro fiber medium and the inner top surface of the container; the space was filled with a nonwoven fabric (50 g/m², thickness of about 1 mm) with a weight of 0.87 g formed of micro fibers made of polyethylene terephthalate with an average fiber diameter of 10 μm. Thus, a plasma separation filter was produced (a volume of the micro fiber medium: 4.0 cm³; a volume of the space: 0.38 cm³).

The total surface area of the micro fibers in the plasma separation filter, the average bulk density, the average hydraulic radius and the pore volume and L/D of the micro fiber medium are shown in Table 1.

The plasma separation was performed using the plasma separation filter in the same manner as in Example 3. After 15 seconds passed from the start of the pressurization, the permeation of liquid was started. The permeated liquid was contaminated by blood cells from the beginning. Thus, the permeated liquid was collected for about 1.5 seconds from the start of the permeation, thus obtaining 0.34 ml of permeated liquid. The average linear velocity was 16.8 mm/min.

The concentrations of leukocytes and platelets in the permeated liquid of 0.34 ml obtained above were below the detection limit. However, the concentration of erythrocytes was $1.1 \times 10^9$/ml. Thus, the erythrocyte remaining amount was 15%. The hemoglobin concentration in the plasma obtained was below the detection limit. The analysis results of the blood components are omitted.

TABLE 1

|  |  | Example 1 | Example 2 | Example 3 | Example 4 | Example 5 | Example 6 | Example 7 | Example 8 | Centrifugation |
|---|---|---|---|---|---|---|---|---|---|---|
| Container shape |  | Disk | Disk | Cylinder | Disk | Cylinder | Cylinder | Cylinder | Cylinder | — |
| Type of micro fiber medium |  | Nonwoven | Nonwoven | Nonwoven | Nonwoven | Mass | Mass | Mass | Mass | — |
| Average fiber diameter | μm | 1.8 | 1.8 | 0.8 | 3.0 | 1.8 | 0.8 | 3.2 | 1.8 | — |
| Total surface area (A) | m² | 2.3 | 1.3 | 4.3 | 1.9 | 2.3 | 4.3 | 1.8 | 1.3 | — |
| A per 1 ml blood |  | 0.57 | 0.33 | 1.07 | 0.47 | 0.57 | 1.07 | 0.45 | 0.33 | — |
| Filling amount | g | 1.4 | 0.8 | 1.2 | 2.0 | 1.4 | 1.2 | 2.0 | 0.8 | — |
| Volume | cm³ | 3.9 | 3.9 | 4.0 | 4.0 | 4.0 | 4.0 | 4.0 | 4.0 | — |
| Average bulk density | g/cm³ | 0.36 | 0.21 | 0.30 | 0.50 | 0.35 | 0.30 | 0.50 | 0.20 | — |
| Average hydraulic radius | μm | 1.28 | 2.51 | 0.72 | 1.32 | 1.32 | 0.72 | 1.41 | 2.65 | — |
| Pore volume | ml | 2.89 | 3.32 | 3.13 | 2.55 | 2.99 | 3.13 | 2.55 | 3.42 | — |
| Blood flow passage length (L) | mm | 25 | 25 | 6 | 65 | 22 | 6 | 51 | 22 | — |
| Blood flow passage diameter (D) | mm | 20 | 20 | 29 | 12.5 | 15.2 | 29 | 10 | 15.2 | — |
| L/D |  | 1.25 | 1.25 | 0.21 | 5.20 | 1.45 | 0.21 | 5.10 | 1.45 | — |
| Pressure | kg/cm² | 0.2 | 0.2 | 0.4 | 0.4 | 0.4 | 0.4 | 0.4 | 0.4 | — |
| Blood amount | ml | 4.0 | 4.0 | 4.0 | 4.0 | 4.0 | 4.0 | 4.0 | 4.0 | — |
| Average linear velocity for treatment | mm/min. | 75 | 100 | 12 | 32.5 | 4.4 | 0.41 | 11.6 | 8.8 | — |
| Starting time for permeation | sec. | 20 | 15 | 30 | 120 | 300 | 880 | 264 | 150 | — |
| Plasma permeation time | sec. | 2 | 1.5 | 3 | 12 | 30 | 90 | 22 | 17 | — |
| Plasma collection amount | ml | 0.29 | 0.33 | 0.31 | 0.26 | 0.30 | 0.31 | 0.26 | 0.34 | — |
| Erythrocyte contamination ratio | % | ≦0.003 | 0.004 | ≦0.003 | 0.04 | ≦0.003 | ≦0.003 | 0.06 | 0.03 | ≦0.003 |
| Erythrocyte hemolysis |  | Absence | Absence | Absence | Absence | Absence | Absence | Absence | Absence | Absence |
| Hemoglobin concentration | mg/dl | 5 | ≦3 | 8 | 4 | 6 | 10 | ≦3 | ≦3 | ≦3 |
| Serum amylase | IU/dl | 292 | 297 | 285 | 297 | 286 | 283 | 296 | 299 | 297 |
| Total cholesterol | mg/dl | 114 | 115 | 110 | 114 | 110 | 108 | 112 | 111 | 114 |
| Neutral fat | mg/dl | 14 | 10 | 10 | 12 | 11 | 7 | 8 | 9 | 8 |
| Urea nitrogen | mg/dl | 16 | 14 | 14 | 16 | 15 | 13 | 15 | 15 | 15 |
| Blood sugar | mg/dl | 594 | 596 | 598 | 602 | 589 | 597 | 603 | 597 | 599 |

|  |  | Comparative example 1 | Comparative example 2 | Comparative example 3 | Comparative example 4 | Comparative example 5 | Comparative example 6 |
|---|---|---|---|---|---|---|---|
| Container shape |  | Disk | Disk | Cylinder | Cylinder | Disk | Cylinder |
| Type of micro fiber medium |  | Nonwoven | Nonwoven | Nonwoven | Mass | Nonwoven | Nonwoven |
| Average fiber diameter | μm | 2.5 | 1.0 | 1.8 | 1.8 | 1.8 | 1.8 |
| Total surface area (A) | m² | 0.9 | 5.8 | 2.3 | 2.3 | 2.3 | 1.4 |
| A per 1 ml blood |  | 0.23 | 1.45 | 0.57 | 0.57 | 0.57 | 0.35 |
| Filling amount | g | 0.8 | 2.0 | 1.4 | 1.4 | 1.4 | 0.87 |
| Volume | cm³ | 3.9 | 3.9 | 3.9 | 4.0 | 3.9 | 4.0 |
| Average bulk density | g/cm³ | 0.21 | 0.54 | 0.36 | 0.35 | 0.36 | 0.22 |
| Average hydraulic radius | μm | 3.58 | 0.39 | 1.28 | 1.32 | 1.28 | 2.37 |
| Pore volume | ml | 3.32 | 2.45 | 2.89 | 2.99 | 2.89 | 3.36 |
| Blood flow passage length (L) | mm | 25 | 25 | 2 | 80 | 25 | 4.2 |
| Blood flow passage diameter (D) | mm | 20 | 20 | 50 | 8 | 20 | 35 |
| L/D |  | 1.25 | 1.25 | 0.04 | 10.00 | 1.25 | 0.12 |
| Pressure | kg/cm² | 0.2 | 0.4 | 0.4 | 0.4 | 0.2 | 0.4 |
| Blood amount | ml | 4.0 | 4.0 | 4.0 | 4.0 | 0.5 | 4.0 |
| Average linear velocity for treatment | mm/min. | 150 | 1.1 | 8.0 | 2.5 | — | 16.8 |
| Starting time for permeation | sec. | 10 | 1365 | 15 | 1920 | — | 15 |
| Plasma permeation time | sec. | 1 | 1600 | 1.5 | 3600 | — | 1.5 |
| Plasma collection amount | ml | 0.33 | 0.26 | 0.30 | 0.25 | — | 0.34 |

TABLE 1-continued

| | | | | | | | |
|---|---|---|---|---|---|---|---|
| Erythrocyte contamination ratio | % | 5.3 | ≤0.003 | 55 | ≤0.003 | — | 15 |
| Erythrocyte hemolysis | | Absence | Presence | Absence | Presence | — | Absence |
| Hemoglobin concentration | mg/dl | ≤3 | 95 | ≤3 | 75 | — | ≤3 |
| Serum amylase | IU/dl | — | — | — | — | — | — |
| Total cholesterol | mg/dl | — | — | — | — | — | — |
| Neutral fat | mg/dl | — | — | — | — | — | — |
| Urea nitrogen | mg/dl | — | — | — | — | — | — |
| Blood sugar | mg/dl | — | — | — | — | — | — |

Example 9

A nonwoven fabric formed of micro fibers made of polyethylene terephthalate with an average fiber diameter of 1.5 μm was cut to have a weight of 2 g, a diameter of 50 mm. and a thickness of 2.0 mm, and was placed in the same disk-like container as used in Example 1 with a space of 1.0 mm between the inner surface of the container and the outer surface of the micro fiber medium. At this point, an average hydraulic radius was 0.64 μm.

Bovine blood having a hematocrit of 45% with an ACD liquid added as an anticoagulant was supplied from an outer circumferential portion to an inside portion at a pressure of 0.5 kg/cm$^2$. The blood passed through the micro fiber medium in the horizontal direction with respect to the nonwoven fabric face in the container, and then plasma was permeated from the outlet about 30 seconds later. The plasma was continuously permeated for about 45 seconds, and thereafter blood cells began to contaminate the plasma. Thus, plasma without contamination by blood cells was collected for 45 seconds after 30 seconds from the start of the pressurization. The total amount was 0.7 ml. The hemoglobin concentration in the obtained plasma was 3 mg/dl or less, and hemolysis was not observed. The concentrations of erythrocytes, leukocytes and platelets measured by a blood cell analyzer were all below the detection limit. Biochemical analysis values of the obtained plasma are shown in Table 2. No significant difference was observed between the permeated liquid at the early stage of collection, the permeated liquid at the time of completion of the collection, a sample of 0.25 ml which is equivalent to a 10% of the pore volume of the micro fiber mediums, and plasma obtained by centrifugation of the same blood. When a fibrinogen in the obtained plasma was measured by cellulose acetate electrophoresis, the result showed that the concentration was reduced to about 30% of the concentration in the plasma obtained by centrifugation. Although fibrinogen was not completely removed, after the obtained plasma was kept for 24 hours, the coagulation of fibrin was not observed.

Example 10

The same filter as used in Example 9 and human blood with a hematocrit of 47% immediately after being collected were used. An anticoagulant was not added to the blood. The blood was supplied to the filter at a pressure of 0.5 kg/cm$^2$. The blood passed through the micro fiber medium in the horizontal direction with respect to the nonwoven fabric face in the container, and thus about 35 seconds later liquid was started to be permeated. Then, the contamination by blood cells in permeated liquid occurred after 55 seconds from the start of the pressurization. Thus, the permeated liquid without contamination by blood cells was collected for 20 seconds after 35 seconds passed from the start of the pressurization. The total amount obtained was 1.0 ml. The hemoglobin concentration in the obtained permeated liquid was 3 mg/dl or less, and hemolysis was not observed. The concentrations of erythrocytes, leukocytes and platelets measured by a blood cell analyzer were all below the detection limit. Biochemical analysis values of the obtained permeated liquid are shown in Table 2. No significant difference was observed between the permeated liquid at the early stage of collection, the permeated liquid at the time of completion of the collection, a sample of 0.25 ml which is equivalent to a 10% of the pore volume of the micro fiber mediums, and serum components obtained by centrifugation of the same blood after coagulation. Furthermore, fibrinogen was not detected in the obtained permeated liquid. The obtained liquid was not plasma, but serum. A fibrinogen in the plasma obtained by centrifugation of the blood added with heparin as an anticoagulant collected from the same subject was 220 mg/dl.

Although an experiment was conducted in the same manner as in the Example 1 except that the human blood was used, a difference in the amounts of the permeated liquid collected was observed. It is believed that this is because the size of erythrocytes is different between bovine and a human. Furthermore, the reason why fibrinogen was completely removed was that an anticoagulant was not added so that fibrinogen was adsorbed to the filter.

Example 11

Nonwoven fabrics formed of micro fibers made of polyethylene terephthalate used in Example 9 were immersed in a solution of 0.1% polyvinyl pyrolidone k-90 (trade name: colidon K 90 manufactured by BASF, MW 360 kd), and irradiated with γ rays of 50 KGy while maintaining a wet state. The γ ray irradiated nonwoven fabrics were washed with pure water to remove uncrosslinked polyvinyl pyrolidone and dried, thus obtaining nonwoven fabrics with polyvinyl pyrolidone immobilized to the surface. The nonwoven fabrics were placed in the container so as to separate plasma in the same manner as in Example 10. The blood moved in parallel to the stacked face of the nonwoven fabrics in the container, and plasma was permeated from the outlet about 15 seconds later. The blood cells began to contaminate the plasma after about 25 seconds passed since the start of the pressurization. Thus, plasma without contamination by blood cells was collected for 10 seconds. The total amount obtained was 1.2 ml. The hemoglobin concentration in the obtained plasma was 3 mg/dl or less, and hemolysis was not observed. The concentrations of erythrocytes, leukocytes and platelets measured by a blood cell analyzer were all below the detection limit. Biochemical analysis values in the obtained plasma are shown in Table 2. No significant difference was observed between the permeated liquid at the early stage of collection, the permeated liquid at the time of completion of the collection, a sample of 0.25 ml which is equivalent to a 10% of the pore volume of the micro fiber mediums, and serum components obtained by centrifugation of the same blood after coagulation.

When a fibrinogen in the obtained plasma was measured by cellulose acetate electrophoresis, the result showed that the concentration was reduced to about 20% of the concentration in the plasma obtained by centrifugation, and fibrinogen was not completely removed. However, after the obtained plasma was kept for 24 hours, the coagulation of fibrin was not observed. By fixing polyvinyl pyrolidone to the micro fibers, the affinity of the blood with respect to the micro fibers is improved, thus reducing a resistance when the blood passed through the micro fibers. Thus, a period of time during which the plasma was separated and permeated was shortened.

Comparative Example 7

A glass fiber filter paper (a fiber diameter: 0.8 to 2.5 μm) was cut to obtain a square of about 2 by 2 mm, and was added with water. Thereafter, the resultant paper was stirred by a mixer and dehydrated in order to be placed in a syringe container of 5 ml as shown in FIG. 4 to a density of 0.5 g/cm². At this point, an average hydraulic radius was 1.45 μm (specific gravity of the glass fiber: 2.2). Bovine blood having a hematocrit of 45% with an ACD liquid added as an anticoagulant in the same manner as in Example 9 was supplied from the top of the container at a pressure of 0.5 kg/cm². The blood passed through the micro fiber medium from the upper portion to the lower portion in the container, and then plasma was permeated from the outlet about 60 seconds later. The plasma was continuously permeated for about 30 seconds, and thereafter the plasma was contaminated by blood cells. Thus, plasma without contamination by blood cells was collected for 30 seconds after 60 seconds from the start of pressurization. The total amount obtained was 0.2 ml. The hemoglobin concentration in the obtained plasma was 3 mg/dl or less, and hemolysis was not observed. The concentrations of erythrocytes, leukocytes and platelets measured by a blood cell analyzer were all below the detection limit. Biochemical analysis values in the obtained plasma are shown in Table 2. The permeated liquid at the early stage of collection, the permeated liquid at the time of completion of the collection, 0.2 ml sample as obtained, and plasma obtained by centrifugation of the same blood were compared. The reason why the 0.2 ml sample as obtained was used is that a sample of 0.25 ml which is equivalent to a 10% of the pore volume of the micro fiber medium was not able to be obtained. The total protein concentration in the permeated liquid at the early stage of collection was significantly lower than the others, and values of electrolytes and lipid were different from those of the plasma obtained by centrifugation. It is believed that this is because protein, electrolytes and lipid were adsorbed to the glass fibers, and electrolytes were partially eluted from the glass fibers to the plasma. When a fibrinogen in the obtained plasma was measured by cellulose acetate electrophoresis, the results showed that the concentration was reduced to about 30% of the concentration in the plasma obtained by centrifugation. Although fibrinogen was not completely removed, after the obtained plasma was allowed to stand for 24 hours, the coagulation of fibrin was not observed.

Comparative Example 8

Nonwoven fabrics formed of micro fibers made of polyethylene terephthalate having a fiber diameter of 3.5 μm were placed in a quantity of 2.4 g in the same container as in Example 1. At this point, an average hydraulic radius was 1.13 μm. Blood was supplied in the same manner as in Example 1. The liquid was permeated from about 45 seconds later, but the permeated liquid contained erythrocytes from the beginning. Thus, plasma was unable to be separated. It is believed that this is because the fiber diameter was as large as 3.5 μm, whereby the transformation degree of erythrocytes was small when erythrocytes passed through the fiber gap, and thus preventing a difference in the moving rates between erythrocytes and plasma.

TABLE 2

|  |  | Example 9 | | | Example 10 | | | Example 11 | | |
| --- | --- | --- | --- | --- | --- | --- | --- | --- | --- | --- |
| Container shape | | Disk | | | Disk | | | Disk | | |
| Type of micro fiber medium | | Nonwoven | | | Nonwoven | | | Nonwoven | | |
| Micro fiber material | | PET | | | PET | | | PET + PVP | | |
| Fiber diameter | μm | 1.5 | | | 1.5 | | | 1.5 | | |
| Total surface area (A) | m² | 3.9 | | | 3.9 | | | 3.9 | | |
| Filling amount | g | 2 | | | 2 | | | 2 | | |
| Volume | cm³ | 3.9 | | | 3.9 | | | 3.9 | | |
| Average bulk density | g/cm³ | 0.51 | | | 0.51 | | | 0.51 | | |
| Average hydraulic radius | μm | 0.64 | | | 0.64 | | | 0.64 | | |
| Pore volume | ml | 2.45 | | | 2.45 | | | 2.45 | | |
| Blood flow passage length (L) | mm | 25 | | | 25 | | | 25 | | |
| Blood flow passage diameter (D) | mm | 20 | | | 20 | | | 20 | | |
| L/D | | 1.25 | | | 1.25 | | | 1.25 | | |
| Blood | | Bovine | | | Human | | | Human | | |
| Pressure | kg/cm² | 0.5 | | | 0.5 | | | 0.5 | | |
| Average linear velocity for treatment | mm/min. | 50 | | | 42 | | | 60 | | |
| Starting time for permeation | sec. | 30 | | | 35 | | | 25 | | |
| Plasma collection amount | ml | 0.7 | | | 1.0 | | | 1.0 | | |
| Blood cell contamination ratio | % | ≦0.003 | | | ≦0.003 | | | ≦0.003 | | |
| Erythrocyte hemolysis | | Absence | | | Absence | | | Absence | | |
| Hemoglobin concentration | mg/dl | ≦3 | | | ≦3 | | | ≦3 | | |
| Type of permeate | | Plasma | | | Serum | | | Plasma | | |
| Permeated liquid | | Earlier stage | Final stage | 0.25 | Earlier stage | Final stage | 0.25 | Earlier stage | Final stage | 0.25 |
| Urea nitrogen | mg/dl | 13 | 13 | 13 | 13 | 12 | 13 | 14 | 13 | 13 |
| Total protein | g/dl | 6.7 | 6.8 | 6.8 | 6.6 | 6.8 | 6.7 | 6.7 | 6.6 | 6.7 |
| Albumin | g/dl | 3.5 | 3.5 | 3.5 | 4.4 | 4.5 | 4.5 | 4.4 | 4.4 | 4.4 |

TABLE 2-continued

| | | | | | | | | | |
|---|---|---|---|---|---|---|---|---|---|
| Total cholesterol | mg/dl | 114 | 115 | 112 | 167 | 165 | 167 | 166 | 168 | 167 |
| Creatinine | mg/dl | 1.5 | 1.5 | 1.5 | 0.9 | 0.8 | 0.8 | 0.9 | 0.9 | 0.9 |
| Cl | mEq/dl | 77 | 78 | 78 | 104 | 102 | 102 | 103 | 104 | 103 |
| Na | mEq/dl | 169 | 170 | 169 | 143 | 143 | 143 | 143 | 142 | 143 |
| K | mEq/dl | 5.1 | 5.3 | 5.3 | 4.7 | 4.7 | 4.7 | 4.7 | 4.5 | 4.6 |
| Ca | mEq/dl | 7.5 | 7.3 | 7.5 | 9.1 | 9.2 | 9.2 | 9.2 | 9.3 | 9.2 |

| | | Comparative example 7 | Comparative example 8 | Blank 1 | Blank 2 |
|---|---|---|---|---|---|
| Container shape | | Disk | Disk | | |
| Type of micro fiber medium | | Nonwoven | Nonwoven | | |
| Micro fiber material | | Glass | PET | | |
| Fiber diameter | μm | 0.8~2.5 | 3.5 | | |
| Total surface area (A) | m² | 2.2 | 2.0 | | |
| Filling amount | g | 2 | 2.4 | | |
| Volume | cm³ | 3.9 | 3.9 | | |
| Average bulk density | g/cm³ | 0.51 | 0.62 | | |
| Average hydraulic radius | μm | 1.37 | 1.13 | | |
| Pore volume | ml | 3.00 | 2.16 | | |
| Blood flow passage length (L) | mm | 25 | 25 | | |
| Blood flow passage diameter (D) | mm | 20 | 20 | | |
| L/D | | 1.25 | 1.25 | | |
| Blood | | Bovine | Bovine | Bovine | Human |
| Pressure | kg/cm² | 0.5 | 0.5 | | |
| Average linear velocity for treatment | mm/min. | 17 | | | |
| Starting time for permeation | sec. | 90 | | | |
| Plasma collection amount | ml | 0.2 | | | |
| Blood cell contamination ratio | % | ≦0.003 | | | |
| Erythrocyte hemolysis | | Absence | | | |
| Hemoglobin concentration | mg/dl | ≦3 | | | |
| Type of permeate | | Plasma | No collection | Plasma | Serum |

| | | Earlier stage | Final stage | | | |
|---|---|---|---|---|---|---|
| Permeated liquid | | | | 0.20 | | |
| Urea nitrogen | mg/dl | 12 | 13 | 13 | 13 | 13 |
| Total protein | g/dl | 4.5 | 6.8 | 5.5 | 6.8 | 6.6 |
| Albumin | g/dl | 2.3 | 3.7 | 3.2 | 3.6 | 4.4 |
| Total cholesterol | mg/dl | 89 | 94 | 93 | 122 | 173 |
| Creatinine | mg/dl | 1.5 | 1.3 | 1.5 | 1.4 | 0.9 |
| Cl | mEq/dl | 89 | 84 | 86 | 75 | 102 |
| Na | mEq/dl | 190 | 193 | 192 | 164 | 144 |
| K | mEq/dl | 3.5 | 4.0 | 3.8 | 5.0 | 4.5 |
| Ca | mEq/dl | 8.5 | 9.0 | 8.9 | 7.6 | 9.4 |

Example 12

Figure 8:
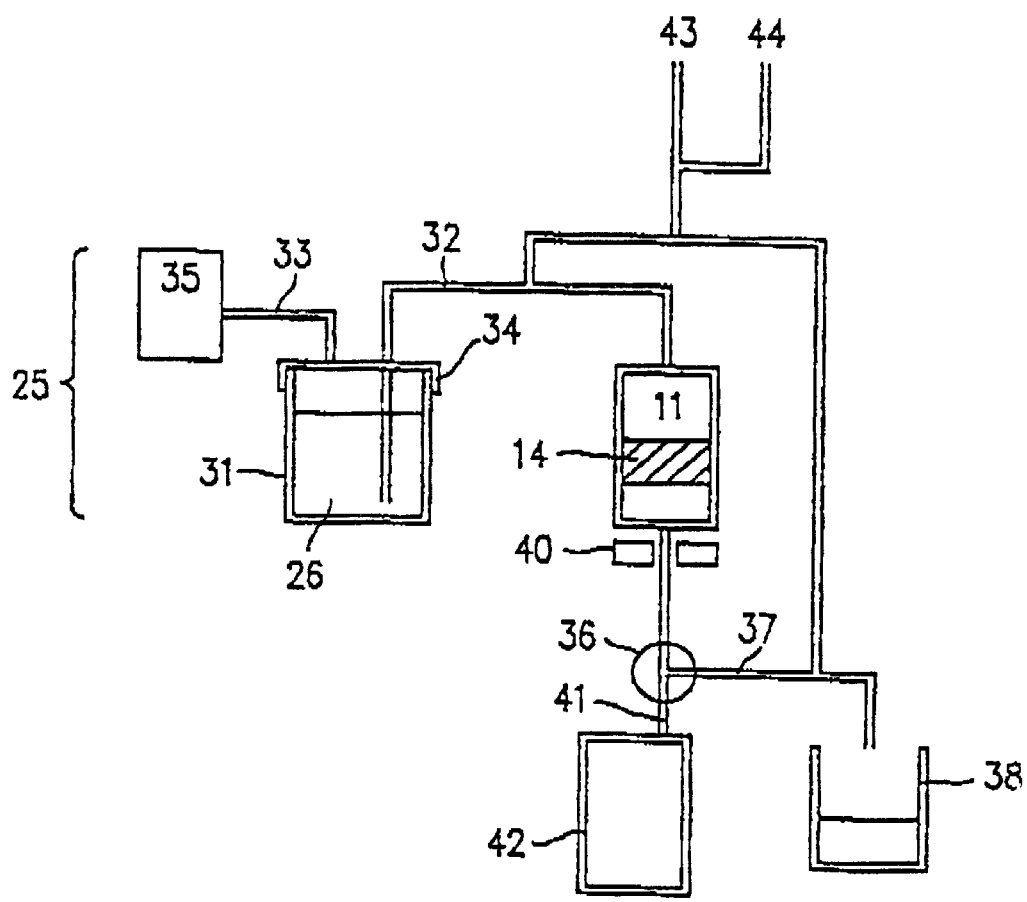
FIG. 8 is a schematic view illustrating an exemplary plasma separation apparatus according to the present invention.

FIG. 8 is a schematic view illustrating an exemplary structure of an apparatus according to the present invention. A container 31 accommodates a blood sample. The container 31 is connected to a plasma separation filter 11 via a line (or tube) 32 for supplying blood. The container 31 is also connected to a supplying line 33 for supplying pressured air.

The container 31 includes a airtight, releasable lid 34. The container 31 can further include a stirring means or shaking means. The container 31 or the line 32 can include a line for supplying an anticoagulant (not shown in FIG. 8).

Blood 26 in the container 31 is pushed out by the pressured air transported through the line 33 from a compressor 35, and is supplied to the filter 11 through the line 32. The pressure of the pressured air is controlled by the compressor 35.

The blood supplied to the filter 11 passes through a micro fiber medium 14 by the pressure caused by the pressure air supplied to the. container 31. During the course of passing through the micro fiber medium 14, the blood is separated into plasma and blood cells. Plasma emitted from the side of a permeated liquid in the filter 11 passes through a line (or tube) 37 for collecting plasma via a three way cock 36, and is collected in a container 38 for accommodating a sample plasma.

A blood cell and/or hemoglobin detector 40 for detecting the contamination by blood cells and/or hemoglobin is provided in the side of the permeated liquid in the filter 11. In addition to the blood cell and/or hemoglobin detector 40, a sampling opening for detecting the contamination by blood cells and/or hemoglobin by a method using chemical reaction or by a cell counter can be further provided. When blood cells and/or hemoglobin are detected in plasma, the three way cock 36 (e.g., possibly a three port valve openable by an electromagnetic function) is switched so that the permeated liquid is transported to a disposal liquid (or draining) tank 42 via a disposal liquid (or draining) line 41. At the same time, the supply of the pressured air to the container 31 is stopped, thus completing the plasma separating operation.

These means can be connected to the blood cell and/or hemoglobin detector, so that, for example, when blood cells and/or hemoglobin are detected, the plasma separation operation can be automatically stopped.

Furthermore, the blood transporting line 32 and a plasma transporting line 37 can include a pure water supplying line 43 for supplying a pure water as cleaning water, and a dry air supplying line 44 for supplying dry air in order to dry the apparatus. In addition, examples of methods for cleaning the apparatus of the present invention include a method of mechanically brushing glass instruments or the like with a rotating brush, a method using a cleaner employing jet current, i.e, flowing water current under high pressure through a nozzle, and a method using ultrasonic waves. These cleaning methods can be used independently or in combination. The above-mentioned methods enables the lines to be speedily cleaned and dried after completing the plasma separation operation, and the next blood sample to be subsequently treated.

Each of the lines constituting the plasma separation apparatus can include various members such as a cock for switching a current direction of liquid, a chamber and a pressure sensor (not shown in FIG. 8) other than the three way cock 36.

Figure 5:
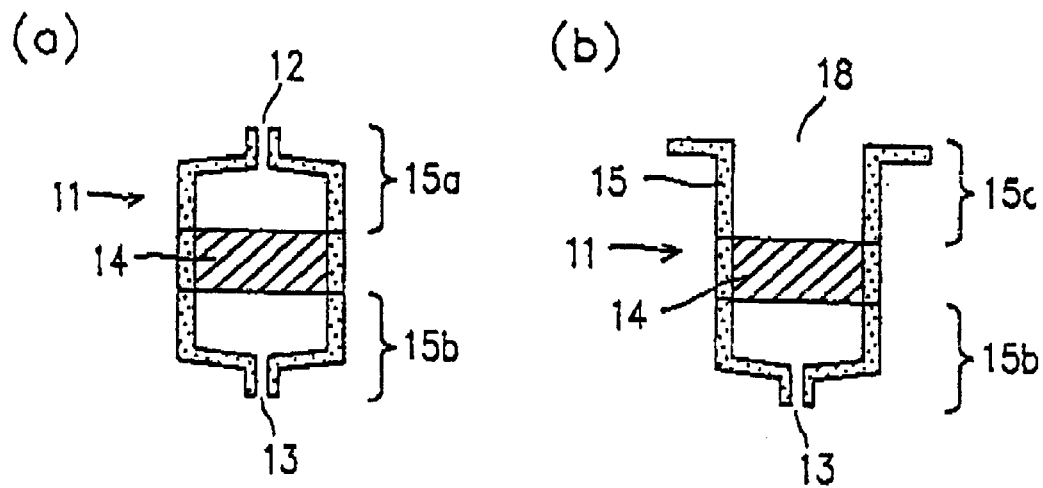
FIGS. 5a and 5b are views illustrating exemplary filters used in a plasma separation apparatus according to the present invention.

The filter 11 can be releasably provided in a holder (e.g., see FIG. 5). A magnet can be used for retaining and releasing the filter 11. The filter 11 can include an inlet portion (15a in FIGS. 5a and 5b), an outlet portion (15b in FIGS. 5a and 5b) and a micro fiber medium (14 in FIGS. 5a and 5b) each of which can be releasably provided. By releasably providing a portion including the micro fiber medium, the micro fiber medium can be disposable, thus preventing contamination. Moreover, the releasability of the portion including the micro fiber medium can make cleaning and drying of the lines efficient.

The apparatus of the present invention can include a structure capable of automatically supplying a blood sample in a predetermined amount to the filter for separating plasma. For example, a quantitative pump can be used to serve this purpose. Furthermore, the apparatus can include a structure capable of automatically exchanging the filter or each component thereof (such as the portion including the micro fiber medium). Furthermore, the apparatus can be obtained by replacing a plasma separator (micro fiber medium) portion of a conventional plasma separation apparatus by the above-mentioned portion including the micro fiber medium or the filter. In addition, when improvement of separation performance is desired, the filter can be connected in series, whereas the filter can be connected in parallel when an amount of blood to be treated is desirably increased.

Example 13

Figure 9:
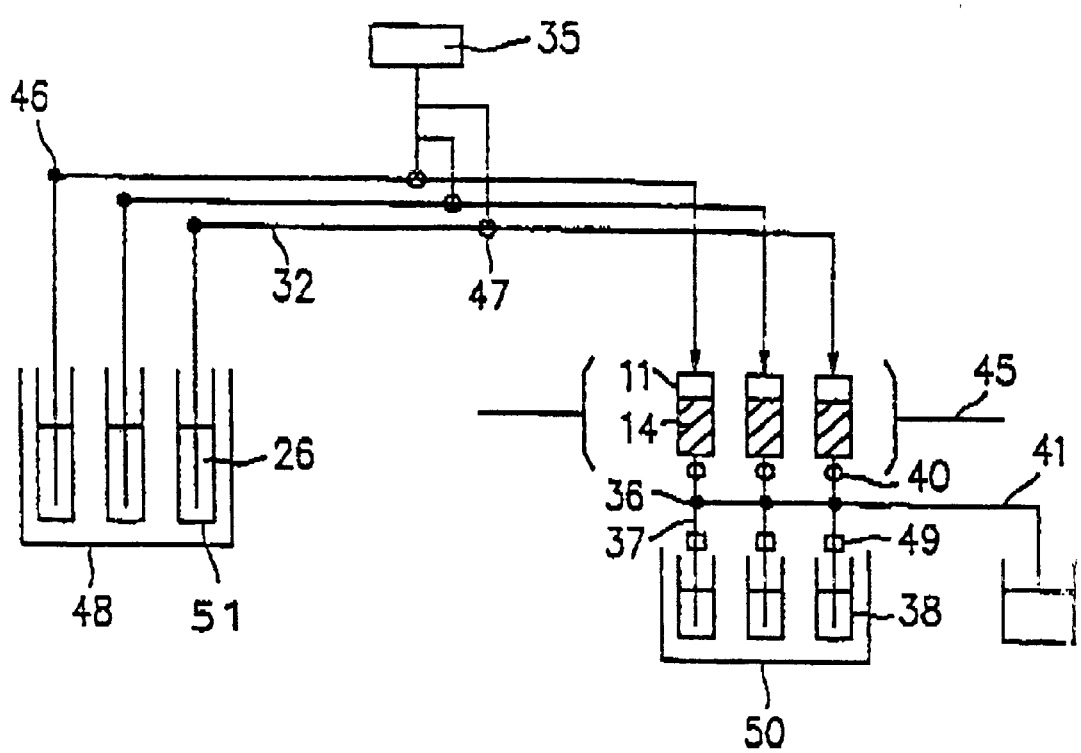
FIG. 9 is a schematic view illustrating an exemplary structure automating the plasma separation apparatus according to the present invention.

The apparatus of the present invention can be automated in the precesses from blood supply to collection of plasma from a large amount of blood samples. For example, FIG. 9 is a schematic view illustrating an exemplary structure for automating the apparatus. By the automation, a number of types of blood samples can be simultaneously treated.

In FIG. 9, blood samples 26 are arranged on a lack 48, and inlets of blood supplying lines 32 are located substantially at the bottoms of the blood samples 26. Filters 11 are fixed in a filter holder 45. The ends of the blood supplying lines 32 are airtightly engaged with the inlets of the filters 11 by pressing the ends of the blood supplying lines 32 with a mechanical force. Similarly, the ends of plasma collecting lines 37 are airtightly engaged with the outlets of the filters 11 by pressing the ends of the plasma collecting lines 37 with a mechanical force. Then, at the outlet of the lines, sample containers 38 for collecting plasma are automatically arranged on a lack 50.

In this manner, the lines are connected, and when the sample containers for receiving plasma are arranged, blood supplying pumps 46 working as blood supplying means are operated. When a predetermined amount of blood is supplied, the blood supplying pumps stop the operation. When the blood supplying pumps 46 are stopped, valves 47 close the blood supplying lines 32. When all the blood supplying pumps 46 are stopped, a compressor 35 is operated, and pressurized air is supplied from the compressor 35 to the filters 11. The blood passes through a micro fiber medium 14 by air pressure, and plasma is separated.

Blood cell and/or hemoglobin detecting means 40 is located at the outlets of the filters 11. When blood cells and/or hemoglobin are detected, three way cocks 36 working as blood cell and/or hemoglobin switching means located downstream of the blood cell and/or hemoglobin detecting means 40 are switched to guide plasma containing blood cells and/or hemoglobin to a blood cell and/or hemoglobin contaminated plasma draining line 41. At the same time, the air supply valves 47 are switched to stop the pressurization. When blood cells and/or hemoglobin are detected, the sample container containing blood cells and/or hemoglobin is marked and a next sample is prepared.

Liquid quantity meters 49 are located at the ends of the plasma collecting lines 37. When a predetermined amount is collected, the switching means 36 is switched to guide unnecessary plasma to the blood cell and/or hemoglobin contaminated plasma draining line 41. At the same time, the air supply valves 47 are switched to stop the pressurization. All the valves are switched, the compressor 35 is stopped.

The lines at the ends of the plasma collecting means are extracted from the sample containers 38 with plasma therein, and the sample containers 38 are closed with lids for preservation.

The inlets of the filters 11 and the ends of the blood supplying lines 32 airtightly engaged with the filters are detached by a mechanical force. The outlets of the filters 11 and the ends of the plasma collecting lines 37 airtightly engaged with the filters 11 are also detached by a mechanical force. The filters 11 detached from respective means are released from the filter holder and disposed of.

Then, cleaning of lines is performed. Hollow containers capable of being airtightly engaged with the ends of the blood supplying lines 32 and the ends of the plasma collecting lines 37 are arranged in place of the filters 11. Containers for receiving cleaning solution are automatically arranged at the outlets of the lines 37 at the ends of the plasma collecting means. The lack 48 where the blood sample supplying containers 51 are arranged is moved when blood supply is completed, and the blood sample supplying containers 51 are disposed of. In place of the blood sample supplying containers 51, containers with cleaning solution therein are arranged on the lack 48, and placed such that the inlets of the blood supplying lines 32 are located substantially at the bottoms of the cleaning solution.

Then, the valves 47 are switched to supply the cleaning solution, and the blood supplying pumps 46 are operated to clean the lines 32, 37 and 41. The valves 36 working as switching means are switched to guide the cleaning solution to the plasma collecting lines 37 and the blood cell and/or hemoglobin contaminated plasma draining line 41 to clean the lines.

After completing the cleaning, the compressor 35 is operated to supply air, and thus drying the lines for a predetermined period of time. Thereafter, the lack 48 where containers with the cleaning solution therein are placed, and the lack 50 where the containers having received the cleaning solution are moved. The containers in the lacks 48 and 50 are replaced by the blood samples and the containers for collecting plasma. Then, the lacks 48 and 50 are positioned back to the predetermined positions. Furthermore, the filters 11 are arranged in place of the hollow containers for cleaning. In this manner, the above-mentioned procedure is repeated.

The order of the those operations can be arbitrarily changed. The method for collecting cleaning solution is not limited to the above-mentioned method. Individual containers are not necessarily used. In any case, an arbitrary change in such an automatic apparatus can be encompassed in the present invention.

Example 14

The apparatus of the present invention generally includes at least (A) a filter, blood supplying means, blood pressurizing means and plasma collecting means. In addition to such means, (a) means for supplying blood in a predetermined amount, (b) means for collecting plasma in a predetermined amount, (c) means for detecting blood cells and/or hemoglobin, (d) switching means, (e) means for draining plasma contaminated by blood cells and/or hemoglobin are arbitrarily combined with the abovementioned means. In the apparatus of the present invention, each means can be operated in connection with other means. Furthermore, each means can be operated in connection with means for stopping the operation thereof. The combination of such means can be arbitrarily changed depending on the use purpose of plasma, a desired level of the plasma, a scale of the apparatus. For example, a typical apparatus is obtained in the following combination: (1) an apparatus including (a) in addition to (A); (2) an apparatus including (b) in addition to (A); (3) an apparatus including (a) and (b) in addition to (A), wherein a sample can be speedily and easily obtained by supplying blood and collecting plasma in a predetermined amount in accordance with types of filter to be used; (4) an apparatus including (c), (d) and (e) in addition to (A), wherein (c), (d) and (e) can be operated in connection with each other; (5) an apparatus including (b), (c), (d) and (e) in addition to (A); (6) an apparatus including all (a) through (e) in addition to (A), which is an example capable of most accurately performing plasma separation among the apparatuses of the present invention.

The average linear velocity for treatment (an average linear velocity for treatment from the inlet to the outlet of the filter) of blood according to the plasma separation apparatus of the present invention is not particularly limited, but preferably 0.5 to 500 mm/min. A low linear velocity for treatment is not suitable for treating a number of specimens, and a too high linear velocity for treatment possibly causes hemolysis due to an increase in a differential pressure.

Example 15
(Connection to automatic analysis system)

An "automatic analysis system" refers to systematization by orderly integrating operations in processes of blood analysis. Namely, it is a system where processes such as collection of specimens, analysis of the specimens and record of data are all automated. The automatic analysis system is classified into two types of system, i.e., a flow system and a discrete system depending on the analysis methods. The plasma separation apparatus of the present invention can be connected to such systems. More specifically, in the flow system, several parts are connected by polyethylene tubes, and a sample is analyzed and recorded while the sample is transported through the tubes. The apparatus of the present invention can be connected to the sampler part of this system. On the other hand, the discrete system is a system in which an individual specimen is analyzed in an independent reaction tube, and the apparatus of the present invention can be connected to the sampler part, as in the flow system. Alternatively, the plasma discretely obtained by the apparatus of the present invention may be used as a sample, and supplied to these automatic analysis system. In this case, a conventional automatic analysis system can be used as it is. The sampler part of the automatic analysis system can be connected to the plasma separation apparatus of the present invention, for example, to the plasma collecting line 37 of the apparatus shown in FIG. 9.

Example 16

A syringe including blood supplying means and a pressurizing means is provided in the plasma separation filter of Example 1, thus producing the plasma separation apparatus shown in FIG. 7.

The bovine blood was injected in an amount 4 ml from the inlet of the container to fill the space between the outer surface of the micro fiber medium and the inner surface of the container, and then a pressure of 0.2 kg/cm$^2$ was applied to push out the bovine blood. The bovine blood entered from the outer surface of the micro fiber medium and moved from the outer portion to the center portion of the inside of the micro fiber medium in a horizontal direction. After 20 seconds passed from the start of the pressurization, the permeation of plasma from the outlet of the container was started. The separated plasma is continuously sampled. Then, the plasma without contamination by erythrocytes was obtained in an amount of 0.5 ml. An average linear velocity for treatment was 75 mm/min. (=25 mm/20 sec.).

The plasma in an early stage of permeation was collected in an amount of 0.4 ml, and subjected to analysis in terms of concentrations of blood cells (erythrocytes, leukocytes, platelets) contained in the plasma, the presence or absence of hemolysis of erythrocytes and blood cell components (serum amylase, total cholesterol, neutral fat, urea nitrogen, blood sugar) to evaluate the apparatus. The results are shown in Table below.

TABLE 3

|  | Example | Comparative Example |
| --- | --- | --- |
| Erythrocyte contamination ratio % | 0.003 | 0.003 |
| Erythrocyte hemolysis | absence |  |
| Hemoglobin concentration mg/dl | 5 | 3 |
| Serum amylase IU/ml | 292 | 297 |
| Total cholesterol mg/dl | 114 | 114 |
| Neutral fat mg/dl | 14 | 8 |
| Urea nitrogen mg/dl | 16 | 15 |
| Blood sugar mg/dl | 594 | 599 |

In view of the detection limit, the ratio of the erythrocyte concentration of the obtained plasma to the erythrocyte concentration of the bovine blood without separation was 0.003% (=2×10$^5$÷7.2×2×10$^9$)×100) or less. Hemolysis of erythrocytes was not caused, and the hemoglobin concentration in the obtained plasma was 5 ml/dl, which is within the acceptable range. The analysis results of the blood components were not different from those of the conventional centrifugation method. Thus, the effectiveness of the present invention was established.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A plasma separation filter comprising a micro fiber medium in a container having an inlet and an outlet and a disk shape, wherein
    (1) the micro fiber medium is made of polyester, polypropylene, polyamide, or polyethylene, and is in a form of a single- or multi-layered nonwoven fabric shaped like a disk,
        wherein the micro fiber medium comprises a central portion and has plane faces,
        wherein the micro fiber medium is placed in the container with a space between the outer peripheral surface of the micro fiber medium and the inner peripheral surface of the container, and blood flows substantially in parallel to the plane faces, and
        wherein the inlet is formed to communicate with the space such that blood is supplied across the entire plane face of the perimeter of the micro fiber medium, and the outlet is formed such that separated plasma is discharged from the central portion of the micro fiber medium;
    (2) a ratio (L/D) of a blood flow passage length (L) to a blood flow passage diameter (D) of the micro fiber medium is 0.15 to 6;
    (3) an average hydraulic radius of the micro fiber medium is 0.5 to 3.0 $\mu$m; and
    (4) when fresh bovine blood having an erythrocyte concentration of 6 to $8 \times 10^9$/ml is separated at a pressure of 0.2 to 0.4 kg/cm$^2$ and plasma filtrate is collected in an amount equivalent to 10% of a pore volume of the micro fiber medium,
        (a) a ratio of an erythrocyte concentration in the plasma to the erythrocyte concentration in the blood before the separation is 0.1% or less; and
        (b) erythrocytes are not substantially hemolyzed.

2. A plasma separation filter according to claim 1, wherein, when fresh bovine blood having an erythrocyte concentration of 6 to $8 \times 10^9$/ml is separated at a pressure of 0.2 to 0.4 kg/cm$^2$ and plasma filtrate is collected in an amount equivalent to 10% of a pore volume of the micro fiber medium, a difference between an electrolyte concentration in the separated plasma and an electrolyte concentration in the plasma obtained by centrifugation is less than 10%.

3. A plasma separation filter according to claim 1, wherein, when fresh bovine blood having an erythrocyte concentration of 6 to $8 \times 10^9$/ml is separated at a pressure of 0.2 to 0.4 kg/cm$^2$ and plasma filtrate is collected in an amount equivalent to 10% of a pore volume of the micro fiber medium, a difference between a protein concentration in the plasma obtained at the start of filtration, that in the plasma obtained at the end of filtration and that in the plasma obtained by centrifugation is less than 10%.

4. A plasma separation filter according to claim 1, wherein the ratio (L/D) of a blood flow passage length (L) to a blood flow passage diameter (D) of the micro fiber medium is 0.25 to 4.

5. A plasma separation filter according to claim 1, wherein the ratio (L/D) of a blood flow passage length (L) to a blood flow passage diameter (D) of the micro fiber medium is 0.5 to 2.

6. A plasma separation filter according to claim 1, wherein the average hydraulic radius of the micro fiber medium is 0.5 to 2.5 $\mu$m.

7. A plasma separation filter according to claim 1, wherein the average hydraulic radius of the micro fiber medium is 0.5 to 2.0 $\mu$m.

8. A filter according to claim 1, wherein the space has a distance of about 1.0 mm between the outer peripheral surface of the micro fiber medium and the inner peripheral surface of the container.

9. A filter according to claim 1, wherein the space has a distance of about 2.0 mm between the outer peripheral surface of the micro fiber medium and the inner peripheral surface of the container.

10. A filter according to claim 1, wherein the micro fiber medium is pressurized in the container.

11. A plasma separation filter comprising a micro fiber medium in a container having an inlet and an outlet and a disk shape, wherein
    (1) the micro fiber medium is made of polyester, polypropylene, polyamide, or polyethylene, and is in a form of a single- or multi-layered nonwoven fabric shaped like a disk,
        wherein the micro fiber medium comprises a central portion and has plane faces,
        wherein the micro fiber medium is placed in the container with a space between the outer peripheral surface of the micro fiber medium and the inner peripheral surface of the container, and blood flows substantially in parallel to the plane faces, and
        wherein the inlet is formed to communicate with the space such that blood is supplied across the entire plane face of the perimeter of the micro fiber medium, and the outlet is formed such that separated plasma is discharged from the central portion of the micro fiber medium;
    (2) a ratio (L/D) of a blood flow passage length (L) to a blood flow passage diameter (D) of the micro fiber medium is 0.15 to 6;
    (3) an average hydraulic radius of the micro fiber medium is 0.5 to 3.0 $\mu$m; and
    (4) a hydrophilic substance is immobilized to the micro fibers.

12. A plasma separation filter according to claim 11, wherein the hydrophilic substance is immobilized to the surface of the micro fibers.

13. A plasma separation filter according to claim 11, wherein the hydrophilic substance is polyvinyl pyrolidone.

14. A plasma separation filter according to claim 11, wherein, when fresh bovine blood having an erythrocyte concentration of 6 to $8 \times 10^9$/ml is separated at a pressure of 0.2 to 0.4 kg/cm$^2$ and plasma filtrate is collected in an amount equivalent to 10% of a pore volume of the micro fiber medium:
    (a) a ratio of an erythrocyte concentration in the plasma to the erythrocyte concentration in the blood before the separation is 0.1% or less; and
    (b) erythrocytes are not substantially hemolyzed.

15. A plasma separation filter according to claim 11, wherein, when fresh bovine blood having an erythrocyte concentration of 6 to $8 \times 10^9$/ml is separated at a pressure of 0.2 to 0.4 kg/cm$^2$ and plasma filtrate is collected in an amount equivalent to 10% of a pore volume of the micro fiber medium, a difference between an electrolyte concentration in the separated plasma and an electrolyte concentration in the plasma obtained by centrifugation is less than 10%.

16. A plasma separation filter according to claim 11, wherein, when fresh bovine blood having an erythrocyte concentration of 6 to $8\times10^9$/ml is separated at a pressure of 0.2 to 0.4 kg/cm$^2$ and plasma filtrate is collected in an amount equivalent to 10% of a pore volume of the micro fiber medium, a difference between a protein concentration in the plasma obtained at the start of filtration, that in the plasma obtained at the end of filtration and that in the plasma obtained by centrifugation is less than 10%.

17. A filter comprising a micro fiber medium in a disk shaped container having an inlet and an outlet, wherein (1) the micro fiber medium is made of polyester, polypropylene, polyamide, or polyethylene, and is in a form of a single- or multi-layered non-woven fabric shaped like a disk, wherein the micro fiber medium is placed in the container with a space between the outer peripheral surface of the micro fiber medium and the inner peripheral surface of the container, wherein the inlet is formed at a peripheral portion of the container to communicate with the space, and the outlet is formed at the center of the container;

(2) a ratio (L/D) of a blood flow passage length (L) to a blood flow passage diameter (D) of the micro fiber medium is 0.15 to 6; and (3) an average hydraulic radius of the micro fiber medium is 0.5 to 30 $\mu$m.

* * * * *